(12) United States Patent
Adams et al.

(10) Patent No.: US 7,154,599 B2
(45) Date of Patent: Dec. 26, 2006

(54) SPECTROMETER INCORPORATING SIGNAL MATCHED FILTERING

(75) Inventors: Bruce W. Adams, Cloverdale (CA); Peter R. H. McConnell, Vancouver (CA)

(73) Assignee: Joule Microsystems Canada, Inc., Burnaby (CA)

( * ) Notice: Subject to any disclaimer, the term of this patent is extended or adjusted under 35 U.S.C. 154(b) by 468 days.

(21) Appl. No.: 10/489,992

(22) PCT Filed: Sep. 19, 2002

(86) PCT No.: PCT/CA02/01423

§ 371 (c)(1),
(2), (4) Date: Mar. 19, 2004

(87) PCT Pub. No.: WO03/025546

PCT Pub. Date: Mar. 27, 2003

(65) Prior Publication Data
US 2004/0239923 A1 Dec. 2, 2004

(30) Foreign Application Priority Data
Sep. 19, 2001 (CA) .................................. 2357668

(51) Int. Cl.
G01J 3/30 (2006.01)
G01N 21/64 (2006.01)

(52) U.S. Cl. .................... 356/317; 356/326; 250/459.1
(58) Field of Classification Search ................ 356/326, 356/317, 318, 328; 250/458.1–461.2
See application file for complete search history.

(56) References Cited

U.S. PATENT DOCUMENTS

| 5,194,916 A | | 3/1993 | Hayashi |
| 5,323,010 A | | 6/1994 | Gratton |
| 6,157,037 A | * | 12/2000 | Danielson ................ 250/458.1 |
| 6,207,961 B1 | | 3/2001 | Lo et al. |
| 6,825,927 B1 | * | 11/2004 | Goldman et al. ........... 356/317 |
| 7,084,409 B1 | * | 8/2006 | Danielson ................ 250/458.1 |

FOREIGN PATENT DOCUMENTS

| DE | 19617106 | 10/1997 |
| DE | 19709377 | 9/1998 |

* cited by examiner

Primary Examiner—Layla G. Lauchman
(74) Attorney, Agent, or Firm—Gottlieb, Rackman & Reisman

(57) ABSTRACT

An optical system for performing a spectral analysis of test samples is provided. The optical system comprises a photonic energy source, an optical emission processing system, a received light optical processing system, an optical detector and a digital signal processing system. The optical emission processing system transmits one or more illumination wavelengths to a test sample. The received light optical processing system collects and isolates one or more wavelengths received from the test sample and transmits them to an optical detector. The optical detector converts the isolated one or more wavelengths of received electromagnetic radiation into an electrical signal which is transmitted to the digital signal processing system. The digital signal processing system performs matched filtering of the electrical signal received from the optical detector and additionally controls the functionality of the photonic energy source, the optical emission processing system and the received light optical processing system.

13 Claims, 13 Drawing Sheets

SPECTROMETER INCORPORATING SIGNAL MATCHED FILTERING

FIELD OF THE INVENTION

This invention relates to the field of optical detectors, in particular with regard to spectrometers.

BACKGROUND OF THE INVENTION

The are a number of spectrophotometers or spectrometers that are used to detect the spectral characteristics of a test sample. For example, U.S. Pat. No. 4,330,207 discloses a fluorescence spectrophotometer comprising a light source, an excitation side monochromator which makes light from the light source be subjected to spectroscopic analysis for illuminating as actinic light a sample, a fluorescence side monochromator which makes fluorescence light from the sample be subjected to spectroscopic analysis, a detector which detects light from the fluorescence side monochromator, and a scanning means which adjusts both the monochromators to the wavelengths of the actinic light and the fluorescence light to be scanned. These monochromators are arranged in such a way that one of them is automatically set to the location of the peak wavelength value which is detected by itself through a simple and automatic wavelength scanning operation and then the other is wavelength-scanned for excitation spectrum or fluorescence spectrum measurement. This device is designed to detect a range of wavelengths of photonic radiation and saves in a memory means the wavelength having the higher peak value.

In addition, U.S. Pat. No. 5,194,916 describes a fluorescence spectrophotometer which comprises an excitation monochromatic light generating means for irradiating excitation monochromatic light onto a sample to be measured, an emission monochromator for selecting monochromatic light from fluorescent light emitted from the sample, an emission photometer for generating a primary output signal corresponding to the strength of the monochromatic light selected by the emission. monochromator, a filtering means for eliminating noises from the primary output and for generating a secondary output, the filtering means being characterized by a response value; determination means for determining a content of the sample based on the secondary output and a response setting means for setting the response value of the filtering means based on the primary output. A table includes the strength data of the primary signal and the corresponding response value, which are determined before hand through experiments and in some cases this correlation can be determined by a mathematical formula.

A spectrophotometer including a light source operative to emit a beam of light, an optical system for directing the light beam to a sample to be analyzed, and a detector which detects the intensity of the light beam after the beam interacts with the sample is disclosed in U.S. Pat. No. 6,002,477. The light source is operative to emit bursts of light separated by an interval during which no light is emitted. By way of example, a xenon tube may be used for that purpose. The spectrophotometer measures the intensity of the light beam generated by each burst of light after that beam interacts with the sample. Each such light beam may be divided into first and second parts prior to interaction with the sample, and the optical system is arranged to direct the first part to the sample and to direct the second part to a second detector for conducting a reference measurement. A dark signal measurement may be conducted immediately before or after each burst of light. Thus by having a reference signal determining the noise within the system provides a means for isolating the received signal. However, the determination of the reference signal at the time of scanning of the test sample is critical to the functionality of this system, since "dark noise" can change dramatically over very small periods of time.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a spectrometer incorporating signal matched filtering. In accordance with an aspect of the present invention, there is provided an optical system for performing a spectral analysis of test samples comprising: a photonic energy source for emitting electromagnetic radiation, wherein said photonic energy source is controlled by a digital signal processing means; an optical emission processing means for receiving electromagnetic radiation from the photonic energy source and transmitting one or more illumination wavelengths to a test sample, wherein the optical emission processing means is controlled by the digital signal processing means; a received light optical processing means for collecting and isolating one or more wavelengths of received electromagnetic radiation from the test sample and transmitting the isolated one or more wavelengths of received electromagnetic radiation to an optical detector, wherein said received light optical processing means is controlled by the digital signal processing means; an optical detector for sensing and converting the isolated one or more wavelengths of received electromagnetic radiation into an electrical signal; and digital signal processing means for performing matched filtering of the electrical signal received from the optical detector and for controlling the functionality of the photonic energy source, the optical emission processing means and the received light optical processing means.

In accordance with another aspect of the invention, there is provided a system for performing an optical analysis of a fluid comprising: an optical probe including an illumination system including a photonic energy source for emitting electromagnetic radiation and optical devices for directing said electromagnetic radiation towards the test sample, said optical probe further including detector optics for collecting and directing electromagnetic radiation emitted by the test sample towards a photodetector, wherein said optical probe is inserted into a fluid flow or a sample chamber containing a fluid sample; a control means for activating the photonic energy source; a photodetector for sensing and converting the electromagnetic radiation emitted by the test sample into an electrical signal; and a digital signal processing means for performing matched filtering of the electrical signal received from the photodetector, said digital signal processing means further controlling the activation of the photonic energy source and encoding the electromagnetic radiation directed towards the test sample.

DETAILED DESCRIPTION OF THE INVENTION

Definitions

Figure 1:
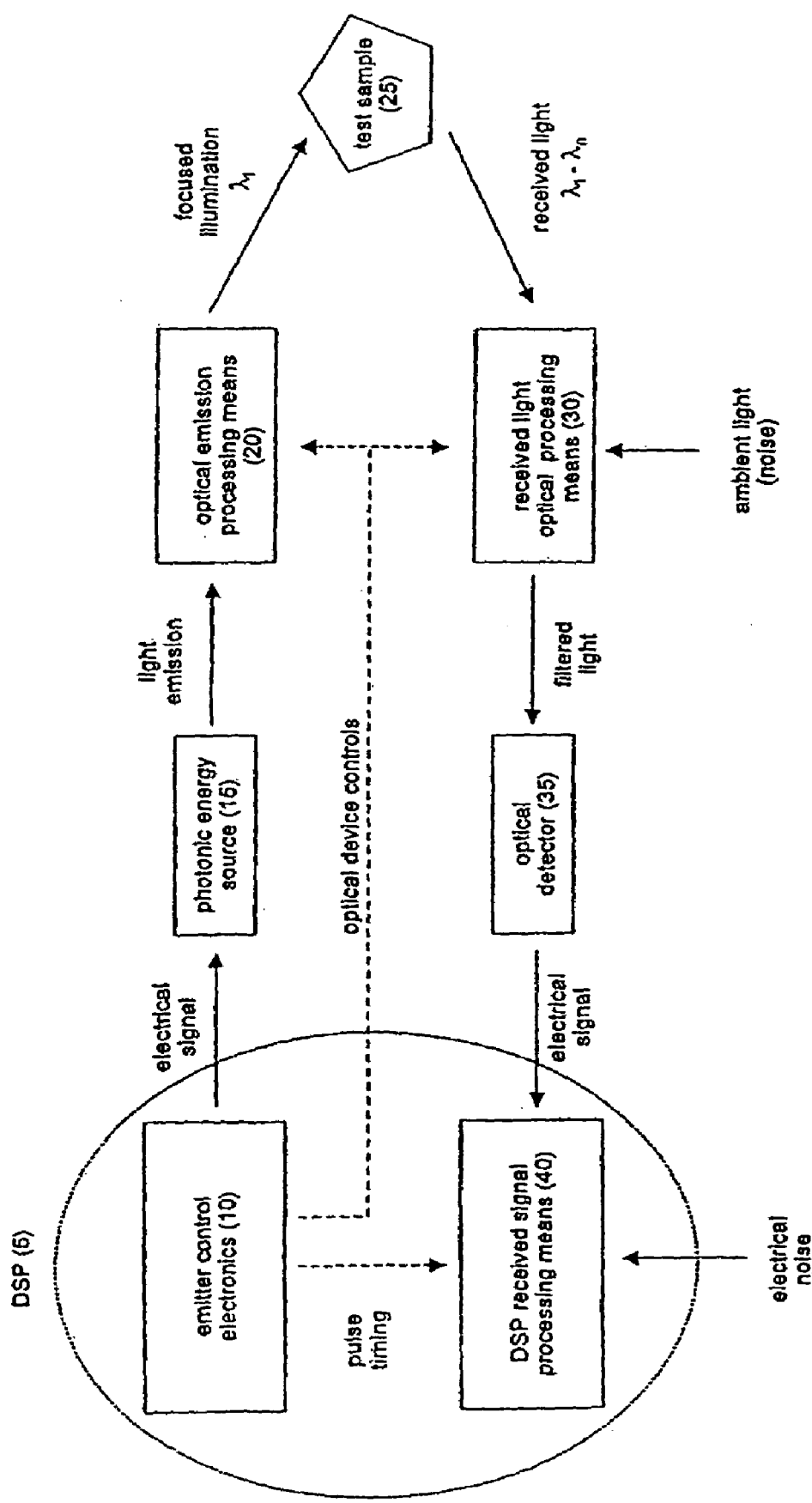
FIG. 1 is a schematic diagram of the optical system components corresponding to one embodiment of the present invention.

The term "electronic light modulator" means an acousto-optic modulator, mechanical light chopper, hologram or electrically driven opto-electonics, or similar devices.

The term "illumination light source" means a light emitting diode (LED), incandescent, laser, gas discharge lamp, laser diode, arc lamp, x-ray source or similar devices.

The term "monochromator" means-a light-dispersing instrument which is used to obtain light of substantially one wavelength, or at least of a very narrow band of the spectrum and may be for example an interference filter, cutoff filter, diffraction prism, diffraction grating, interferometer, hologram or similar devices.

The term "photodetector device" means a light detection device or optical detector and includes a photodiode, photomultiplier, charge couple device (CCD) or similar devices.

The term "resultant radiation" refers to each or all of the reflected, transmitted, absorbed and fluoresced light that result when a subject is exposed to an illuminating radiation.

The phrase "weak signal detection" refers to techniques used to enable measurement of low intensity emission radiation from a sample. For any given signal to noise ratio, the information error rate can be lowered by increasing the bandwidth used to transfer the information. The signal bandwidths are spread prior to transmission in the noisy channel, and then despread upon reception. This process results in what is called Processing Gain.

The term "signal spreading" refers to a number of means of spreading the signal, including Linear Frequency Modulation (sometimes called Chirp Modulation) and Direct Sequence methods and other techniques.

The term "signal despreading" refers to a process that is accomplished by correlating the received signal with a similar local reference signal using a Correlation Receiver or Matched Filter receiver technique. When the two signals are matched, the spread signal is collapsed to its original bandwidth before spreading, whereas any unmatched signal is spread by the local reference to essentially the transmission bandwidth. This filter then rejects all but desired signals. Thus, in order to optimize a desired signal within its interference (thermal noise in the detection system, ambient light induced noise, AC line noise, for example), a matched filter receiver enhances the signal while suppressing the effects of all other inputs, including noise.

Unless defined otherwise, all technical and scientific terms used herein have the same meaning as commonly understood by one of ordinary skill in the art to which this invention belongs.

The various aspects of this invention will become more readily appreciated and better understood by reference to the following detailed description.

The system according to the present invention provides an optical scanning system incorporating optical signal encoding and matched filtering, enabling the detection of the response of a test sample to its illumination, wherein this response can include reflection, fluorescence, transmission and/or absorption. Due to the enhanced signal-to-noise ratio provided by this system, this invention can detect subtle optical changes in a test sample.

With reference to FIG. 1, the optical system of the present invention comprises a spectrometer and a digital signal processing means 5, comprising: a photonic energy source 15 which is controlled by the digital signal processing means 5 (specifically the emitter control electronics 10), to emit electromagnetic radiation which can range from ultraviolet to far infrared (or a bandwidth from 150 nm to 3000 nm) and optical emission processing means 20 which is controlled by the digital signal processing means 5 (specifically the emitter control electronics 10) to receive light from the photonic energy source 15 and to deliver one or more illumination wavelengths in a pulsed sequence to a test sample 25. The optical emission processing means 20 can comprise a means for isolating one or more illumination wavelengths and emitter optics that orient and focus the illumination wavelength(s) onto the test sample 25. The system further comprises received light optical processing means 30 which is controlled by the digital signal processing means 5 (specifically the emitter control electronics 10) to collect and isolate one or more wavelengths of received light due to the illumination of a test sample 25. The received light optical processing means 30 can comprise detector optics for collecting the received light from the test sample 25 and a means for isolating one or more of the wavelengths of the received light. Additionally, the system comprises an optical detector 35 to sense and convert to an electrical signal, the received light which has been transmitted by the received light optical processing means 30 and a DSP received signal processing means 40, which is a component of the digital signal processing means 5, to perfom the match filtering on the output of the optical detector 35. The match filtering of the received signal is performed based on the received electrical signals from the optical detector 35 and control parameters from the emitter control electronics 10.

There are various locations for noise or interference to enter the system according to the present invention, with this interference decreasing the ability to detect signals received from the test sample due to its illumination. For example and with further reference to FIG. 1, ambient light can enter the system through the received light optical processing means 30 and electrical noise can enter the system through the DSP received signal processing means 40. The incorporation of a digital signal processing means can provide a means for the encoding of the illumination signal and the matched filtering of the received signal in relation to the encoded illumination signal. As such, the digital signal processing means can enable improved detection of the received signals resulting from the illumination of the test sample.

Figure 2:
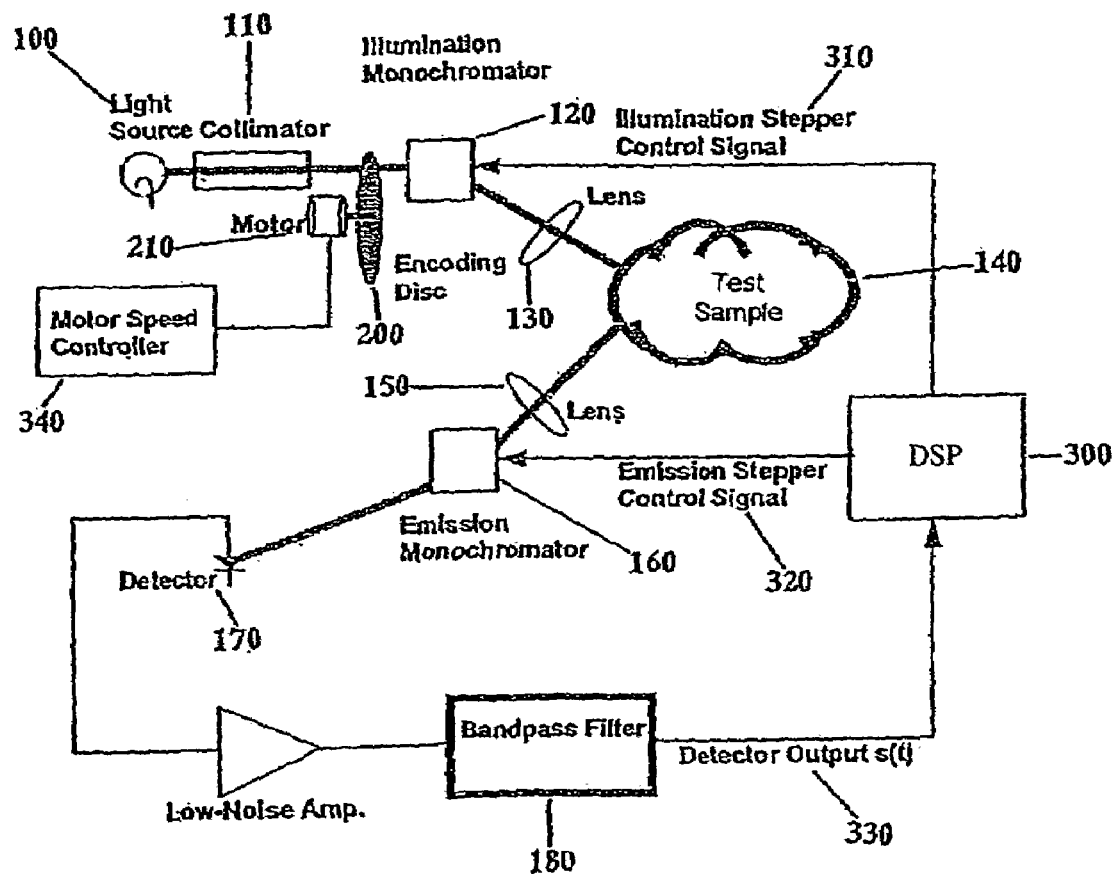
FIG. 2 is a schematic diagram of the optical system according to another embodiment of the present invention.

In order to describe how the components operate together, an overview of one embodiment of a system in accordance with this invention is presented in FIG. 2. In this embodiment an illumination light source 100 is controlled by digital signal processing means 300 to emit a radiation bandwidth ranging from, for example, 250 nm to 1000 nm. A collimator 110 linearises the illumination light and directs it to the light modulator 200, wherein a collimator 110 may be, for example, a long narrow tube in which strongly absorbing or reflecting walls permit only radiation travelling parallel to the tube axis to traverse the entire length. The light modulator 200 which could be an encoding disc (as shown in FIG. 2), acousto-optic modulator, or electronic modulator such that it may enable amplitude or phase modulation, for example, essentially spreading the optical signal. An illumination monochromator 120 is controlled by the digital signal processing means 300 to receive light from the illumination light source 100 and to deliver the $N^{th}$ wavelength in a pulsed sequence to an optical probe which delivers the $N^{th}$ wavelength to the test sample 140, for example, a fluid sample. The resultant radiation, due to the illumination of the test sample, is collected and delivered to the emission monochromator 160. Radiation signals detected from the subject are still encoded with the spread function coding and the intensity is proportional to the reflection coefficient and the fluorescence coefficient. The detection monochromator 160, which is controlled by digital signal processing means 300, separates the reflection and fluorescence spectra optically, by performing specific digital processing tasks to pass the $N^{th}$ wavelength reactive characteristics for a specific illumination wavelength, so that each of these encoded optical signals can be detected by the photo detector 170. The photo detector 170 detects the optical signal and converts it to an electrical signal, which is then processed by the bandpass filter 180, (essentially an Analog to Digital Converter) and transmits it to the digital signal processing means 300. The digital signal processing means 300 performs matched filtering in order to identify and isolate the response of the test sample to the illumination radiation from the noise that enters the optical system from various sources.

Figure 3:
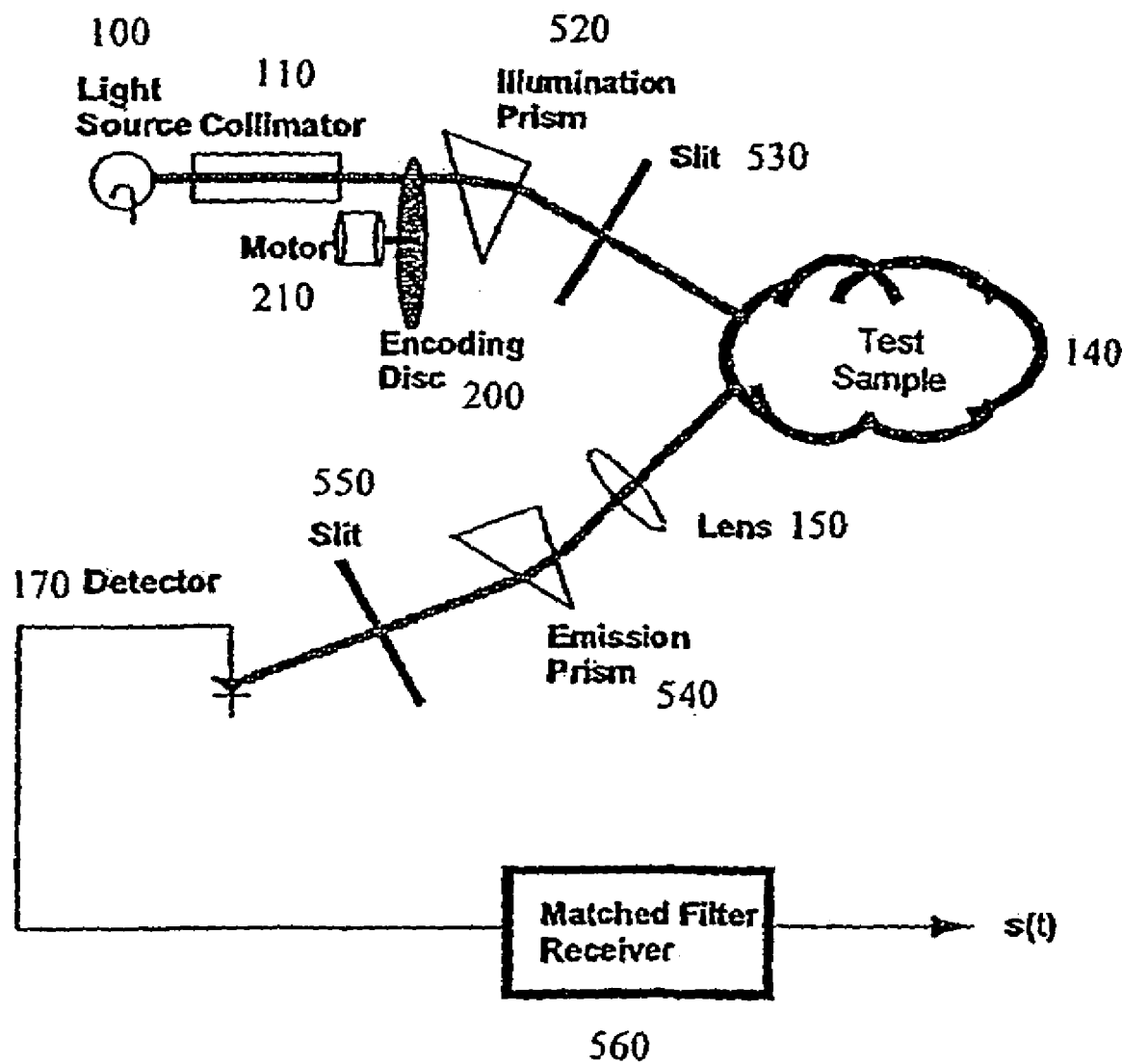
FIG. 3 is a schematic diagram of a scanning spectrometer system according to a further embodiment of the present invention incorporating a Matched Filter Receiver.

In an alternate embodiment the optical system can be configured with the components as illustrated in FIG. 3. A light source 100 generates photonic energy which is directed towards an encoding disc 200 by a collimator 110. The directed encoded photonic energy passes through an illumination prism 520 for separating the various wavelengths of the illumination radiation. The separated illumination radiation is directed towards a slit 530 oriented in a manner such that the desired wavelength or band of wavelengths are transmitted to the test sample 140. The radiation emitted by the test sample 140 as a result of its illumination, is collected by a lens 150 and transmitted to an emission prism 540 wherein the emitted radiation is separated into the various wavelength. The emission prism 540 directs the emitted radiation to a slit 550 oriented in a manner such that the desired wavelength or band of wavelengths is directed towards the detector 170. The detector 170 converts the emission radiation into an electrical signal which is directed to the matched filter receiver 560 for processing the gathered information relating to the illumination of the test sample.

There are a number of embodiments of this optical system, comprising variations of particular components. Each embodiment, however, has a form of each of these components. Some criteria for choosing which component should be included in a particular embodiment is described below.

A Photonic Energy Source

Each embodiment includes a photonic energy source that is controlled by the digital signal processing means to emit electromagnetic radiation which can range from ultraviolet to far infrared (or a bandwidth from 150 nm to 3000 nm).

A photonic energy source which can be used in conjunction with the present invention can be selected from the group comprising: a laser, laser diode, light emitting diode (LED), arc flashlamp, a continuous wave bulb, an electronically controlled flashlamp, any gas discharge lamp or any other photonic energy source as would be known to a worker skilled in the art. The selection of the photonic energy source that is to be used in a particular embodiment of the present invention, can be determined by the required spectral analysis of the test sample. The functionality of the device may require a broad spectral analysis of a test sample or may require the spectral characteristics over a narrow bandwidth or even specific wavelength, for example.

For example, a laser has a very narrow spectrum (a highly coherent "single" wavelength), narrow spatial beam and a high pulsed power. An incandescent light bulb has a broad spectrum, wide beam and continuous transmission.

In one embodiment of the present invention, the electromagnetic radiation generated by the photonic energy source may be in the form of pulsed electromagnetic radiation.

Optical Emission Processing Means

The optical emission processing means receives light from the photonic energy source and may deliver one or more illumination wavelengths in a pulsed sequence to a test sample, wherein the optical emission processing means can comprise a means for isolating one or more illumination wavelengths and emitter optics that orient and focus the illumination wavelength(s) onto the test sample. The optical emission processing means is controlled by the emitter control electronics contained in the digital signal processing means, wherein the emitter control electronics may perform functions comprising pulse coding and pulse shaping, for example enabling the modulation of the illumination energy.

In order to distinguish the light wavelengths due to reflection and fluorescence, which are received from the test sample, from ambient light noise, the illumination of the test sample should be performed using narrowband illumination.

In one embodiment of the present invention a generic device may require the ability to easily vary the illumination spectral characteristics, such that spectral characteristics of the test sample can be determined for a range of illumination wavelengths. This can be accomplished by using a broadband light source, such as a halogen bulb or a Xenon tube and subsequently using wavelength separation optics to filter the emitted light thereby isolating narrow portions of the spectrum for illuminating the test sample. An alternate approach is to use an array of multiple narrowband or mediumband light sources (eg. laser diodes and/or various coloured LED's), each having particular desired spectral characteristics, and subsequently activating them one at a time, thereby effectively traversing a broad spectrum of light and isolating particular illumination wavelengths during the sequence of illumination of these devices.

The optical control processing means further comprises a light control device that provides a means for modulating the light, which is to illuminate the test sample, for example producing a pulsed sequence of light emissions. A light control device can be an indirect light modulator, for example, a light chopper, shutter, liquid crystal filter, galvanometric scanner or acousto-optic device. In addition, light modulation can be performed in a direct manner using an amplitude modulator circuit or a frequency modulator circuit. A worker skilled in the art would understand alternate methods of modulating the illumination light emissions.

The wavelength separation optics can be selected from fixed light conditioning optics including optical filters, refractive optics, diffractive optics and a variable light conditioning subsystem including a refractive or diffractive optical system whereby the optical centre wavelength is chosen by the use of a position controlled reflective surface after the light has passed fixed light conditioning optics. The fixed light conditioning optics may also be a refractive or diffractive optical system whereby the optical centre wavelength is chosen by use of a position controller to move fixed light conditioning optics. An example of a wavelength separation optic device is a monochromator. Other forms of wavelength separation optic devices would be known to a worker skilled in the art.

Emitter optics can be used to transmit the photonic energy between the components of the optical emission processing means and also to transmit the illumination light to the test sample. The emitter optics can be selected from the group comprising, condensers, focusing devices, fibre optics, apertures and other devices as would be known to a worker skilled in the art.

In one embodiment of the invention wherein the analysis of a fluid is desired, for example, a water tight optical probe may be incorporated into the optical system, wherein this optical probe can be inserted into a fluid test chamber. This optical probe comprises components for illuminating the test sample and for collecting the light emitted by the test sample due to its illumination. Since the optical probe is being inserted into the fluid sample, a reduction in the reflection effects of the surface boundary layers of the sample will be realised. In this embodiment, the optical probe comprises the photonic energy source, for example a LED or a laser diode, the illumination optics for directing the illumination radiation to the fluid sample and the detection optics for collecting the reflected and fluoresced light. The optical probe is interconnected with the further components of the optical system, for example the DSP means and the photodetector for the transmission of instructions and collected data therebetween. The illumination optics and the light detection optics can be oriented within the optical probe such that the fluid's interaction with the illumination light can be sufficiently detected. In one embodiment of the invention, the optical probe further comprises a self cleaning feature, for example a wiper mechanism, wherein residue from the fluid which adheres to the surface of the probe can be removed.

Received Light Optical Processing Means

The received light optical processing means collects and isolates one or more wavelengths of received light from the test sample, with this received light being related to the illumination of the test sample as described above. The received light optical processing means can comprise detector optics for collecting the received light from the test sample and a means for isolating one or more of the wavelengths of the received light for detection by the optical detector. The received light optical processing means is controlled by the emitter control electronics contained in the digital signal processing means and thus its function can be correlated with the optical emission processing means, which can provide a means for the efficient analysis of the received spectral emissions.

In one embodiment of the present invention, the received light optical processing means can isolate particular wavelengths of received light by using wavelength separation optics, which provides a means for isolating one or more wavelengths of received light thus allowing the received light to be correlated to the illumination wavelength.

The wavelength separation optics can be selected from fixed light conditioning optics including optical filters, refractive optics, diffractive optics and a variable light conditioning subsystem including a refractive or diffractive optical system whereby the optical centre wavelength is chosen by the use of a position controlled reflective surface after the light has passed fixed light conditioning optics. The fixed light conditioning optics may also be a refractive or diffractive optical system whereby the optical centre wavelength is chosen by use of a position controller to move fixed light conditioning optics. An example of a wavelength separation optic device is a monochromator. Other forms of wavelength separation optic devices would be known to a worker skilled in the art.

In a further embodiment of the present invention, the received optical processing means may be required to isolate one selected wavelength. For example, if the test specimen is illuminated by a particular wavelength of light and the level of reflection of this illumination photonic energy by the test sample, is required, the received optical processing means can have a fixed light separation means. In this manner only a particular received light wavelength is being evaluated.

Detector optics can be used to transmit the photonic energy between the components of the received light optical processing means and also to transmit the received light to the optical detector. The detector optics can be selected from the group comprising, condensers, focusing devices, lenses, fibre optics and apertures. In one embodiment of the invention an optical filter may provide this functionality, wherein the optical filter may include a low pass, high pass band filters or other compatible filters as would be known to a worker skilled in the art.

Optical Detector

Each embodiment includes an optical detector which can sense the light transmitted by the received light optical processing means and convert this received light into an electrical signal for processing by the digital signal processing means and in particular the DSP received signal processing means.

An suitable optical detector can be a diode, photomultiplier, or a charge-coupled device (CCD) arranged in a linear array or an area array, for example. A specific example of an optical detector is a blue enhanced Gallium-Arsenide photodiode, a Cadmium Sulfide (CdS) photodiode or a silicon avalanche diode.

Digital Signal Processing Means

Digital Signal Processing (DSP) means can be used to control the photonic energy source, the optical emission processing means and the received light optical processing means in order to be able to detect one or more wavelengths of the resultant radiation in relation to one or more wavelengths of illumination radiation, wherein this detection is being performed in the presence of noise introduced into the system. The digital signal processing means comprises emitter control electronics, which provide a means for controlling the illumination radiation (optical emission processing system) and the received light optical processing system. In addition, the DSP means comprises a received signal processing means which enables the DSP to correlate the received light radiation with the illumination radiation, which can provide a means for identifying reflectance, fluorescence and absorption from a test sample due to its illumination.

The emitter control electronics which control the illumination radiation performs tasks including: supplying electrical power and driving circuitry to convert electrical energy into light energy, controlling the amplitude and timing of light source pulses, controlling optical devices which filter, focus, or mechanically pulse the illumination radiation, for example, a light filter, monochromator, collimator and/or a chopper. In addition, the emitter control electronics provide a means for controlling the received light optical processing means enabling the isolation of reflectance and fluorescence light wavelengths from the test sample due to its illumination. For example, the incorporation of a monochromator into the received light optical processing means can provide a means for isolating desired wavelengths and the functionality of the monochromator is controlled by the received light optical processing system.

The coding function which is employed by the emitter control electronics in order to encode the illumination signal prior to interaction with the test sample can be provided by any number of signal modulation techniques. For example, pulse code software can be used to create a synchronous pulse for direct modulation of the light control device frequency (pulse frequency modulation, PFM). With PFM the frequency of the pulses is modulated in order to encode the desired information. Pulse code software can be used to create a synchronous pulse for direct modulation of the light control device amplitude (pulse amplitude modulation, PAM), wherein with PAM the amplitude of the pulses is modulated in order to encode the desired information. In addition, pulse code software can be used to create synchronous pulse for direct modulation of the light control device pulse width (pulse width modulation, PWM). With PWM the width of the pulses is modulated in order to encode the desired modulation. Finally the illumination signal may be encoded using a function generator to create a fixed synchronous pulse enabling pulse rate and amplitude modulation, in addition to a mechanical encoder driver to create a synchronous pulse for an indirect light modulator, for example a chopper, shutter, galvomirror etc.

In one embodiment of the invention the coding function which is employed by the emitter control electronics is binary phase shift keying (BPSK) which is a digital modulation format. BPSK is a modulation technique that can be extremely effective for the reception of weak signals. Using BPSK modulation, the phase of the carrier signal is shifted 180° in accordance with a digital bit stream. The digital coding scheme of BPSK is as follows, a "1" causes a phase transition of the carrier signal (180°) and a "0" does not does not produce a phase transition. Using this modulation technique a receiver perform is a differentially coherent detection process in which the phase of each bit is compared to the phase of the preceding bit. Using BPSK modulation may produce an improved signal-to-noise advantage when compared other modulation techniques, for example on-off keying.

The DSP received signal processing means enables matched filter correlation between electrical signals received from the optical detector and the corresponding time period as defined by the emission control electronics. This correlation between transmitted and received signals can provide a means for enhanced identification of received signals over the noise (ambient light or electrical noise, for example) which may enter the optical system of the present invention. Filtering and time averaging of received signals, synchronized and matched with the emitted pulse sequence, enhances the signal-to-noise ratio (SNR) and improves the confidence in the measurement of the sample response at a wavelength or wavelengths of interest.

A matched filter is an exact copy of the signal of interest. The filter is correlated with the input signal, with this procedure basically being a sum of the products of the signal multiplied by the filter over the total duration of the filter. Upon the matching of the filter and the signal of interest, the correlation (convolution) sum typically peaks relative to the non-matched sums providing a means for identifying the signal over the external noise within the optical system. In one embodiment of the present invention, a bank of narrowband filters centered at intervals of the pulse rate can capture more lines from the pulse spectrum, and thus may provide a means for improved light pulse energy estimation and subsequent identification of the detected wavelength.

In one embodiment of the present invention, if the time domain spreading function is represented by $F(\omega)$ and the received signal is represented by $H(\omega)$, then the output of the matched filter receiver can be obtained using the digital signal processor:

$$s(t) = \int_{-\infty}^{+\infty} F(\omega)H(\omega)e^{j\omega t}\, df \quad \text{where: } \omega = 2\pi f$$

In this equation $F(\omega)$ is the Fourier Transform of the input signal $f(t)$ and $H(\omega)$ is the Fourier Transform of the receiver linear filter $h(t)$. In a matched filter, the receiver linear filter $H(\omega)$ is adjusted to optimise the peak signal-to-noise ratio of the receiver output $s(t)$ for a specific input signal $f(t)$. When the receiver linear filter response $H(\omega)$ is given by:

$$H(\omega) = KF^*(\omega)e^{-j\omega t^*}$$

then the output signal-to-noise ratio is maximised and the receiver filter response $H(\omega)$ is matched to the input signal $f(t)$, wherein $f(t)$ has the Fourier Transform $F(\omega)$. The two above equations are taken from "Information Transmission, Modulation and Noise, A Unified Approach to Communication Systems"; Schwartz, Mischa; Third Edition. A matched filter receiver enables one to potentially maximise the signal-to-noise ratio of the output signal $s(t)$, the detection of which is desired. Thus a matched filter receiver may provide optimum detection of the output signal. Since a matched filter receiver is a linear system, $s(t)$ is directly proportional to the intensity of the reflectance and fluorescence illumination on the detector. The use of a matched filter can enable one to detect weak signals in the presence of noise (external and internal noise of the optical system), which may not be detectable using other optical systems.

In one embodiment of the invention, the signal processing system involves both analog front-end and digital back-end tasks. In general the analog processing tasks are concerned with recovering the small sensor signals and applying highly selective filtering operations. The digital domain tasks are concerned with further signal filtering as well as analysis functions, in relation to energy detection and data output. To minimize the interference and to provide immunity against shot noise, the illumination signal is modulated by a frequency of typically a few hundred Hz. The analog section is designed to high gain amplify and prefilter the photodiode output and recover the modulation frequency. Utilizing these signals, a narrowband tracking filter can provide the very high selectivity for modulated signal recovery. The output of the narrowband filter, after amplification, is analog/digital converted and input into a DSP (digital signal processor) which in real time performs the back-end tasks of filtering, energy detection, averaging and converting the results into usable data. The filtering will further enhance the rejection of a/c noise and harmonic distortion, which may have been introduced in the final stages of analog processing. The filtering is followed by an averaging energy detector, which outputs the values proportional to the energy of the sensor signal. These values are sent to the host computer in short intervals, where they can be stored and processed for further analysis.

Figure 4:
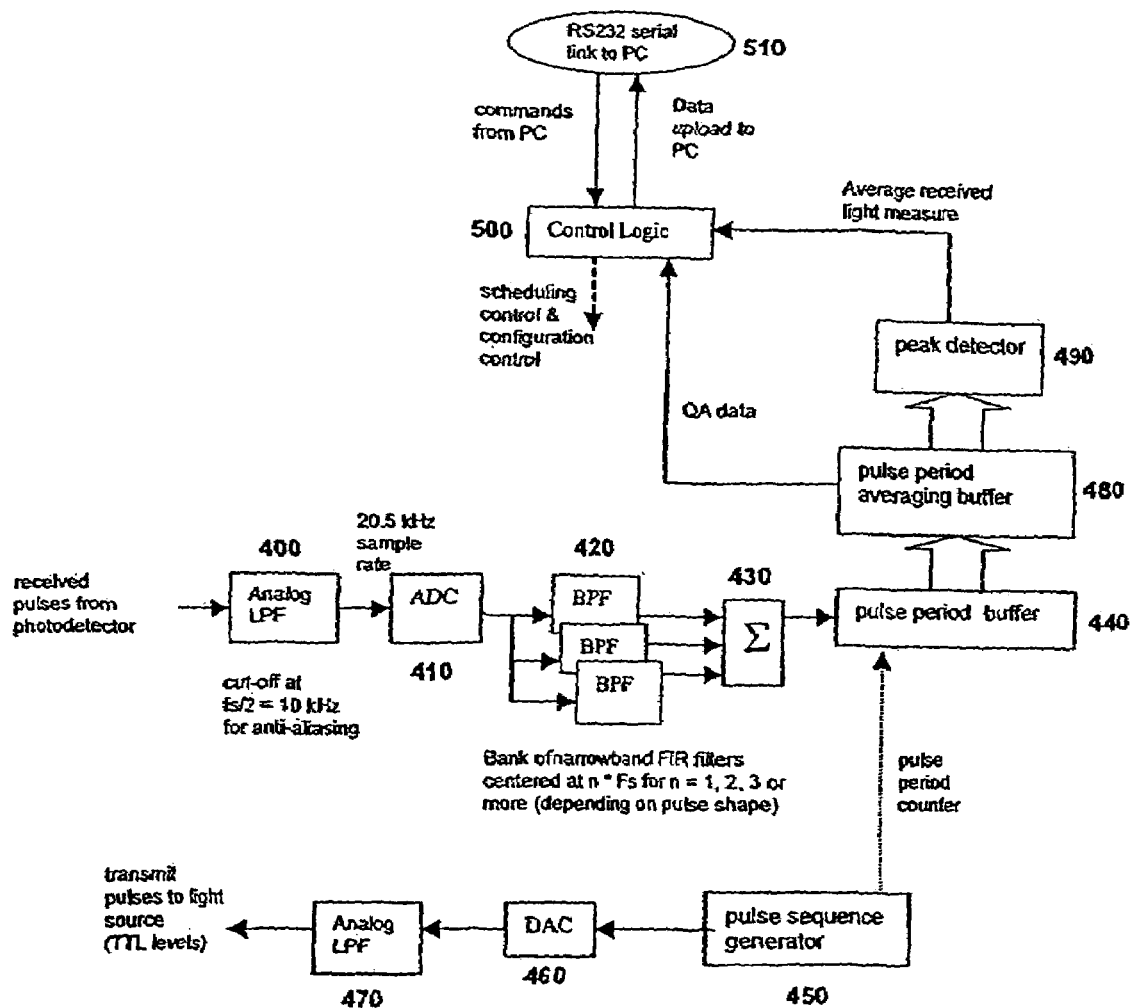
FIG. 4 is a schematic diagram of a digital signal processing means light pulse processing system.

In another embodiment of the present invention, the digital signal processing means can be designed as illustrated in FIG. 4. Initially, a pulse sequence generator 450 transmits a pulse period counter to the pulse period buffer 440 and further transmits a digital signal defining the generated sequence to a digital to analog converter 460. The resulting analog pulses are sent to the light source upon passing through an analog low pass filter 470 and the light source subsequently illuminates the test sample based on these pulses. Upon the collection and detection of the emitted radiation from the test sample due to its illumination, the pulses generated by the photodetector as a result of photonic radiation detection are transmitted to an analog low pass filter (LPF) 400, which transmits the filtered information to a analog to digital converter (ADC) 410. The analog LPF can suppress frequencies over 10 kHz, for example, thereby providing anti-aliasing. This digitized information is sent to a bank of narrowband finite impulse response (FIR) filters 420, wherein each filter is matched to one of the lines in the pulse sequence spectrum (input signal pulse). This provides a means for matching the pulse spectrum in order to identify the signal over the external noise within the system (match filtering). The sums of the filter—input signal correlation 430 are transmitted to the peak detector through pulse period buffers 440 and 480 and the average light measured is then sent to the control logic 500 of the DSP. The control logic 500 provides a means to perform scheduling control and configuration control of the digital signal processing (DSP) means. The averaged measured light signals are subsequently transmitted to a computing device located on a personal computer, for example, via a RS232 serial port 510, in order to be organised into a usable and presentable format, for example generating a graphical representation of the collected information.

In one embodiment of the invention, the functionality of the DSP means may further comprise the ability of establishing an alarm setting, wherein one or more actions are taken upon the activation of an alarm setting. For example, the DSP means may constantly correlate and perform statistical analyses on the processed data and once a predetermined level of change in the received light is reached, the DSP means will activate the alarm setting. The activation of an alarm setting may result in a message being sent to personnel which are monitoring the optical system, for example in the form of a warning light or noise. In one embodiment, wherein the test sample is a flowing fluid sample, the activation of an alarm setting can result in a fluid sample being extracted from the fluid flow, through the use of a valve to transfer fluid from the flow to a collection container, for example. This fluid sample may subsequently be subjected to a detailed analysis for evaluation of its contents at a laboratory, for example. In the example of the monitoring of a flowing fluid, the incorporation of an alarm setting may enable the capturing of significant changes in the fluid contents by the sampling of the fluid upon the detection of a particular level of change in fluid's reaction to light illumination. This procedure can provide an improved evaluation of the changes in a fluid's content as opposed to periodic, time based, sampling of the fluid.

The utilization of advanced signal processing techniques, enables the detection of optical reflectance and fluorescence emissions that would normally not be able to be detected Moreover, the signal processing algorithms can be implemented in standard digital signal processing chips, enabling the overall cost of devices based on this technology to be relatively low.

The DSP means can be incorporated into a computer system in the form of a circuit board that can be installed in a computer, wherein the computer can provide a means for manipulating and organising the received information after matched filtering into a format that is easy to interpret by the operators of the system, for example. Alternately, the DSP may comprise stand alone hardware providing a means for the DSP to function independently.

Stand Alone DSP System

In one embodiment of the present invention, the digital signal processing means together with its sub-systems is designed in a stand-alone configuration. In this type of stand-alone configuration, the DSP system can further include the capability of interconnecting with a global communication system, for example the Internet or for networking within a local area network (LAN). This type of interconnection with a communication network can enable the collection of information from a plurality of test sites by a central station, thereby potentially reducing the personnel required for the collection of this test data.

As would be known to a worker skilled in the art, depending on the communication system (LAN, WAN, Internet) by which the information from the optical systems is transmitted and the desired level of security desired for the information, varying levels of encryption of the data may be required.

In this embodiment the stand alone DSP comprises a transmitter and receiver block, a micro-controller block (MCU), a networking block and a digital and analog power supply block.

In this embodiment the DSP block comprises a digital signal processing chip and an additional external static random access memory (SRAM). The DSP block performs the computation algorithms for fast, real-time processing of spectral data being transferred from the optical detector(s). This block also generates signals that are capable of modulating the photon energy source, wherein this modulation signal can be multiplexed to multiple photon energy sources if required. However, each detector, if there is more than one, has a separate channel into the DSP block for the transmission of information relating to the received light. In addition, the DSP block can control the optical device(s) that mechanically pulse the illumination radiation, for example, a chopper. As would be known to a worker skilled in the art, the required processing speed of the DSP chip can be determined by the estimated amount and frequency of the incoming data that is to be processed, for example. In this manner an appropriate chip can be determined based on its processing speed for example the number of hertz that the DSP operates, 40 Hz, 60 Hz and so on.

According to this embodiment, the transmitter and receiver block comprise analog-to-digital converter(s) (ADC), digital-to-analog converter(s) (DAC) and low-pass filters, wherein these filters enable anti-aliasing of the received signal. If light emitting diodes (LEDs) or laser diodes are used as the photon energy source for the optical system, this block further comprises a multiplexer and high current amplifiers. The multiplexer enables the transmission of signals for the activation of the multiple photon energy sources independently and the high current amplifiers provide a means for providing sufficient energy in order to activate these photon energy sources such that their maximum spectral power output is obtained.

The networking block of the stand alone DSP means comprises a networking card, for example, an ethernet chip or a wireless network chip, which enables the interconnection of the stand alone DSP system to a communication network, for example a local area network (LAN), a wide area network (WAN) or a wireless network (for example Bluetooth™ or IEEE 802.11). A worker skilled in the art would understand the format and type of chip or card that is required for the desired network connection. In addition the network block further comprises a serial interface chip, for example a RS-232 port which can provide a serial interface to another component or system, for example a computer or a serial modem, for example dial-up or wireless type modem or a serial connection to a monochromator.

Furthermore, in this stand alone embodiment, the microcontroller unit (MCU) block comprises a MCU chip, which may be an 8-bit, 16-bit or 32-bit chip, for example, an external SRAM and an external FLASH unit. The MCU block manages the DSP block and the networking block, wherein the MCU block collects processed data from the DSP block and forwards this information to the networking block. Optical devices which filter and/or focus the illumination radiation and received light, for example light filters or monochromators, can be controlled by the MCU block. The MCU block may additionally perform statistical analyses on the data and may possibly activate an alarm setting. For example, an alarm setting may be activated if the level of fluorescence of the test sample exceeds a predetermined level, wherein this alarm activation may comprise the collecting of a sample for a more detailed analysis or the notification of personnel of the alarm activation. In the case where software updates to the DSP block are required, for example the modification of the match filtering procedure, the MCU block can manage the remote software updates of the DSP code, for example. The type of MCU chip incorporated into the MCU block may vary depending on the volume of information that is to be processed for example, as would be known to a worker skilled in the art.

The digital and analog power supply block of the stand alone DSP system can provide regulated DC power at a variety of levels depending on that required by the components of the stand alone DSP system. In one example, the input power to this stand alone system may be supplied by an unregulated or varying power supply, for example a wall plug. The digital and analog power supply block comprises elements which can regulate the input power and subsequently generate the required analog and digital voltage levels for each component of the stand alone DSP system. As examples, elements which enable the adjustment of the input power comprises transformers, AC-DC converters or any other power regulation element as would be known to a worker skilled in the art.

Test Sample Housing

Optionally, the optical system comprises a test sample housing which provides a means for orienting a test sample such that the illumination of the sample and the detection of the samples resultant emissions can be performed. For example, as would be used with a microscope, the test sample housing may comprise a cover slip and a glass plate for securing the test sample and a set of clips may be used to orient and restrain the movement of this glass plate and cover slip during testing.

In one embodiment of the present invention wherein the test sample is a flowing fluid, a test sample housing may be a tube inserted and appropriately oriented within the fluid flow wherein this housing provides a means for an optical probe to be oriented therein. This sample housing can be designed such that it minimises the effects on the flow of the fluid thereby potentially reducing its affects on the detected response of the fluid to its illumination. The size, in particular the cross sectional area, of the test sample housing can be designed such that the surface area of the housing is outside of the optical detector's field of view. In this manner, the detection of reflectance from the housing may be minimised. In order to potentially further reduce the test sample housing's affect of the response, the surface are of the housing can be fabricated using or painted with a non-reflective light absorbing material. Furthermore, the in this embodiment, the test sample housing can be fabricated such that the optical probe can be removed for cleaning, if desired and subsequently replaced in the same orientation. A form of indexing may be used in order to facilitate the realignment of the optical probe upon replacement with in the test sample housing.

Considerations

In one embodiment, the requirements of the optical system are that: 1) it is able to resolve optical spectra over the range 250 nm to 800 nm; 2) the spectral resolution is on the order of 5 nm of better; and 3) that it has a stray light suppression of $10^{-5}$ or better, for both the illumination and emission units. In addition, a spectral resolution of 5 to 10 nm can allow reasonable sampling of the fluorescence peaks, which appear to be the order of 30 to 50 nm. However, finer resolution may be useful in some applications. The stray light suppression factor required depends on how small an area of received light one wishes to detect. Stray light essentially determines the optical noise floor for the system, and sets the limit of optical detectability.

In choosing the illumination wavelength, the factors that should be balanced are overall scanning time for the area of interest or test sample and the resolution of the scan. The total number of steps N required to sweep out the illumination light and received light spectrums is:

$$N = n_i n_d / 2$$

where:

$n_i$=number of steps for the illumination monochromator $n_d$=number of steps for the received light monochromator The factor ½ determines that only the diagonal terms of the illumination light/received light matrix are of interest in addition to the terms on one side of the diagonal only. Moreover, N is proportional to $\Delta\lambda/2$, where $\Delta\lambda$ is the spectral resolution of a monochromator. Since the scanning time is proportional to N, then there is a trade-off between $\Delta\lambda$ and the scanning time.

Weak Signal Detection

In one embodiment, the tone encoded method is used for signal encoding due to its basic simplicity and the fact that it yields a reasonable degree of noise suppression relative to the complexity. In this embodiment, the key consideration is the amount of time required to take one measurement. This is determined by: 1) the amount of time required to acquire the samples for a frequency domain transfer, which is essentially the number of samples required divided by the sample rate and 2) the filter bandwidth in the case of a bandpass filter technique, which is essentially the reciprocal of the bandwidth of the filter.

The trade-off with the electrical signal bandwidth is observation time versus noise. As the bandwidth is increased and the observation time is decreased, the noise power increases in proportion to the bandwidth. Any increase in noise reduces the detector sensitivity. The total processing time to scan the area of interest can be determined by $T=N\tau$, where $\tau$ is the time for one measurement at one wavelength. The two key variables in the observation time are the optical filter bandwidth and the electrical filter bandwidth.

A rough first order calculation of T can be made by making the following assumptions: 1) resolve optical spectra over the range 250 nm to 800 nm; 2) use an optical resolution bandwidth of 10 nm; and 3) use an electrical bandpass filter BW of 10 Hz, therefore $\tau=0.10$ sec. By using these assumptions, the scanning time is 151.25 seconds, or about 2.5 minutes.

When a test sample to be examined is exposed to illuminating radiation, the detection of reactive radiation characteristics is the goal. In general, the fluorescent light will be much weaker than the reflected light. The spectral resolution required is determined by the ability of the optical spectrometer system to discriminate between reflected and fluorescent wavelengths. This may be achieved through the use of a prism and/or grating monochromators with variable apertures, which suppress stray radiation.

For optical signatures to be adequately resolved, the system must be able to detect very weak electrical signals, which result from the optical radiation being detected by the photodiode. Ultimately, the goal is to detect a very weak signal in a background of noise due to electrical noise, optical background radiation and out of band emissions from the test sample (due to the spectrometer spectral resolution).

Other variables in the measurement of spectral signatures comprise: a) time duration the test sample is illuminated; b) the amplitude of the illumination at the test sample first surface; c) the amplitude of the noise variables; d) spectral shifts in the illuminators over time; and e) the decay of the fluorescence emitted by a test sample after the illumination of the test sample has been discontinued. These variables need to be addressed to compare the performance of various detection schemes.

In one embodiment of the present invention, adaptive filtering of the received light may enable the detection of the decaying intensity of fluorescence emitted from a test sample upon the discontinuation of the illumination of the test sample. The discontinuation of the illumination may be complete termination of transmission of photonic energy or the discontinuation of a particular illumination wavelength.

The measurement of the decay of fluorescence emitted by a test sample using a device according to the present invention may provide a means for the identification of a test sample.

Figure 5:
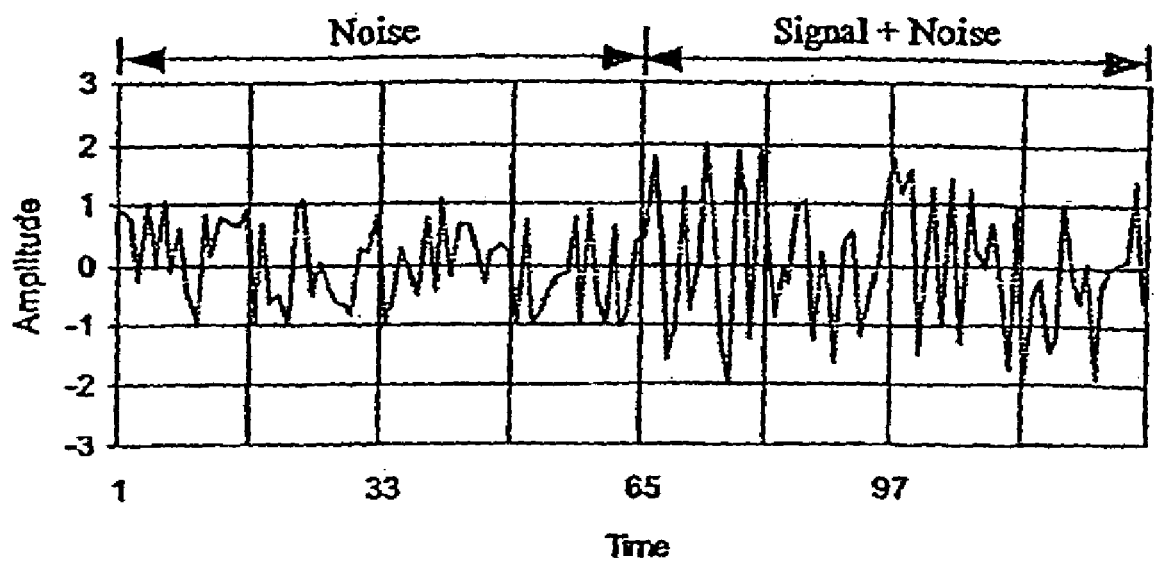
FIG. 5 demonstrates On-Off keyed signal with a 0 dB signal to noise ratio, using pulse amplitude modulation detection.

Pulse amplitude modulation techniques as applied to this situation may be On-Off keying of the illumination. The detection is based on the ability to detect the presence of the signal in an ambient noise. The signal detectability depends on the ability to discriminate the signal from the noise and generally requires a signal power much greater than the noise (>10 dB typically). An example of an On-Off keyed signal is shown in FIG. 5. The signal to noise ratio (SNR) in this case is 0 dB and it is not possible to distinguish the noise portion of the signal from that consisting the signal plus noise.

The frequency domain detection mechanism is a detection means based on frequency modulation of the signal with a constant frequency modulation. This has great advantages over time domain detection means such as On-Off keying. Even though the RMS amplitudes of the signal and the noise can be equal (SNR=0 dB), the power spectral density of the modulated signal is usually much greater than the power spectral density of the broadband noise. The carrier can be isolated from the noise by a number of means, including: a) spectral measurement techniques, such as a DFT or FFT; and b) narrow band filtering with the centre frequency of the filter located at the modulation frequency.

Figure 6:
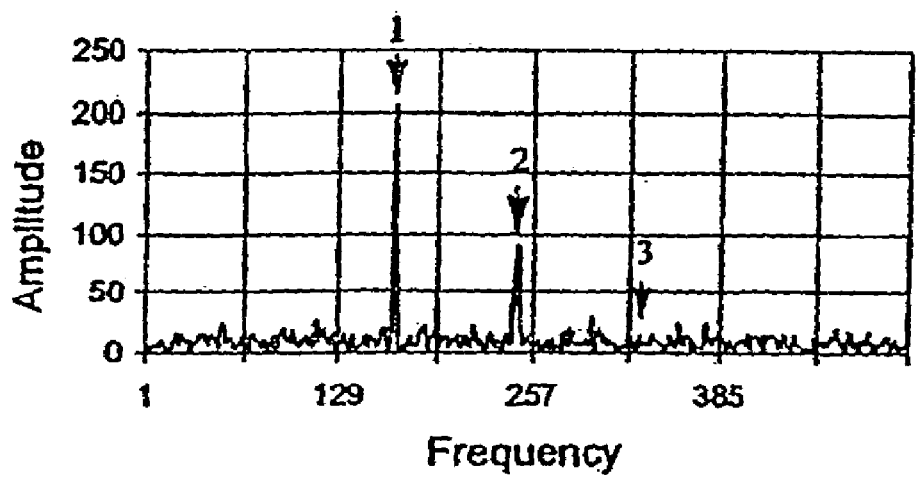
FIG. 6 demonstrates signal detection using frequency domain detection.

An example of this is shown in FIG. 6. In this case, the RMS amplitudes of the first signal and the noise are equal (SNR=0 dB). Two other signals were added which had magnitudes relative to the first signal of 0.50 and 0.1 respectively. The time domain signal happens to look exactly like that shown in FIG. 5. In the frequency domain however, the spectral peaks for the first and second signals are apparent. The spectral signature for this signal is buried in the noise and cannot be resolved. This detection technique is relatively simple to implement in practice and can be suitable for use in an optical spectrometer.

The pulse coding techniques (binary, linear, enhanced) are an alternative means of detection. Pulse coding techniques are often used to detect very weak signals in the presence of noise. They may be more complex than traditional techniques such as tone detection and pulse amplitude detection, however they are sometimes the only choice when amplitude of the signal to be detected is weak relative to the noise and there are no means available to increase the signal to noise ratio other than pulse coding. Two exemplary pulse coding techniques are Binary Pulse Coding and Linear Frequency Modulation (FM) Coding. Both of these techniques fall into the realm of pulse compression and spread spectrum and they are adequately described in numerous references (Barton, DK (1978) Radars Volume 3: Pulse Compression, Artech House Inc.).

Figure 7:
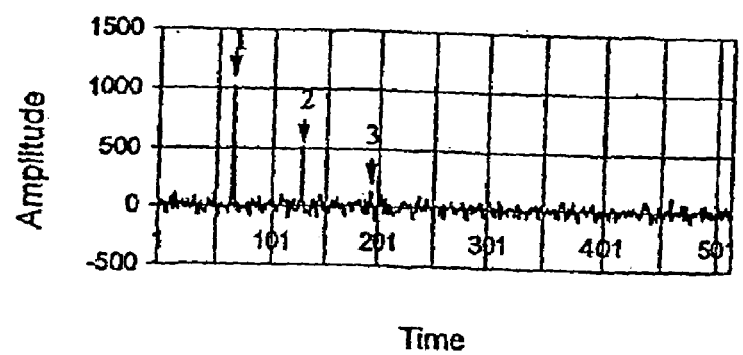
FIG. 7 demonstrates the results of the time domain correlation output from binary pulse coding signal detection.

Binary Pulse Coding, as an example, uses a 1000-bit synchword, which can be created by using a uniform random number generator and constructing a binary sequence from that data. Pulses are generated at specific locations in the time domain and the relative amplitudes are measured. Results of a time domain correlation output are shown in FIG. 7. In an amplitude plot, all three pulses can be detected. The third and smallest signal pulse is just distinguishable from the noise.

Figure 8:
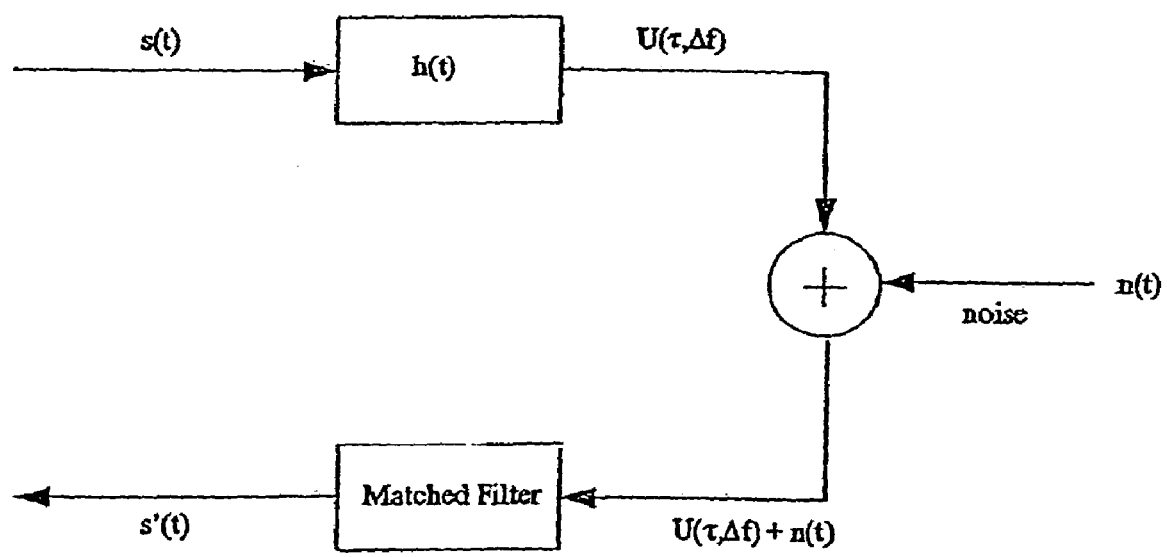
FIG. 8 is a schematic representation of a pulse coding channel model.
Figure 9:
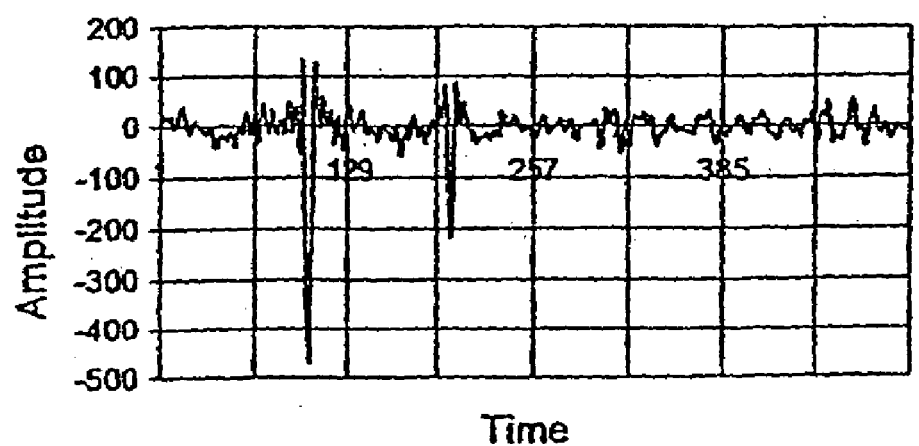
FIG. 9 depicts the detector output using a linear FM Chirp, which is a 125 msec wide rect function, swept from 500 Hz to 3500 Hz and sampled at 8000 samples/sec.

Linear FM Pulse Compression schemes have traditionally been used in radar systems to reduce the overall peak power of transmitted signals while still achieving large detection ranges. They also figure prominently in Synthetic Aperture Radar processing for airborne and spaceborne imaging radars. This form of coding is achieved by linearly sweeping a carrier signal from $f_1$ to $f_2$ (for a swept bandwidth of $\Delta f$) for a duration $\tau$. In general, the "output power" of a linear FM coded signal is increased by the Time Bandwidth Product (TBP) $\Delta f\tau$, which is the product of the pulse duration in seconds and the swept bandwidth in Hertz. The detection process is essentially a matched filter detector, which is matched to the linear FM transmitted pulse. The overall process is shown in FIG. 8. The signal s(t) is usually a Dirac Delta function, which in reality is simply the trigger pulse for the encoder h(t) which generates the transmitted signal $U(\tau,\Delta f)$ which is the linear FM coded pulse (or Chirp) which has a duration $\tau$ and a bandwidth $\Delta f$. This is the signal that would drive an optical emitter to illuminate a test sample. Noise n(t) is added to the coded signal in both the optics and the electronics. This optical signal is detected by a photodetector, whose electrical output signal is comprised of the actual optical signal of interest, optical background noise and electrical noise in the photodetector and electronics. The matched filter detector then processes this electrical signal. Since the optical signal of interest is the only one of the three components of the signal which is matched to the matched filter, it is the only component which experiences gain due to the linear FM pulse coding. The optical and electrical noise components are essentially suppressed relative to the coded signal. This is an advantage of such a scheme. A linear FM Chirp output is shown in FIG. 9. In the amplitude plot, only the largest two pulses can be detected, with the third being essentially buried in the noise. This example graphically demonstrates the coding gain offered by a linear FM Pulse Compression Technique.

Enhanced Pulse Coding Techniques take advantage of the fact that by increasing the Time Bandwidth Product, greater coding gain can be achieved. Using this technique the weakest of the time domain pulses was just visible.

Figure 10:
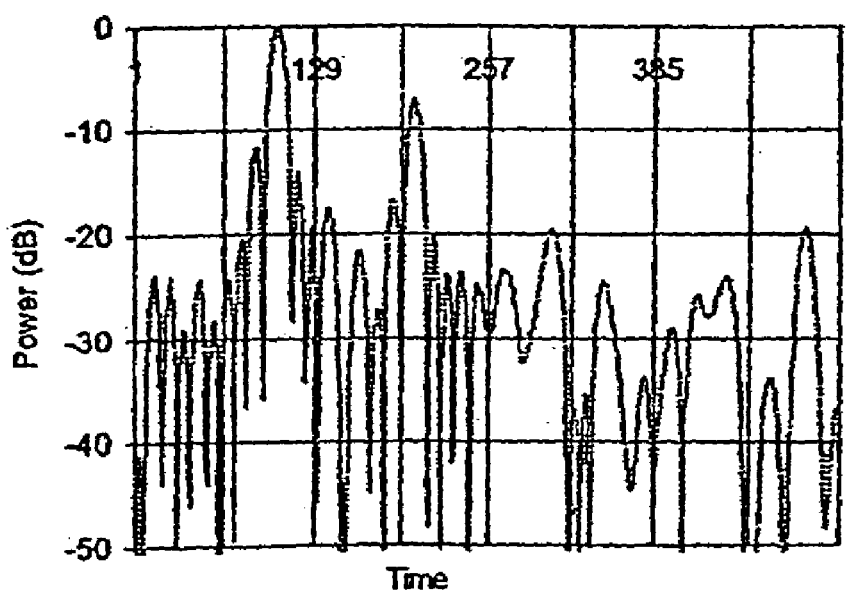
FIG. 10 demonstrates the use of a linear FM pulse coding technique where the pulse duration was left at 0.125 seconds and the bandwidth was 1600 Hz for a time bandwidth product (TBP) of 200. A log scale of the detector was calculated as; P=20×log s, where s is the time domain output of the matched filter.
Figure 11:
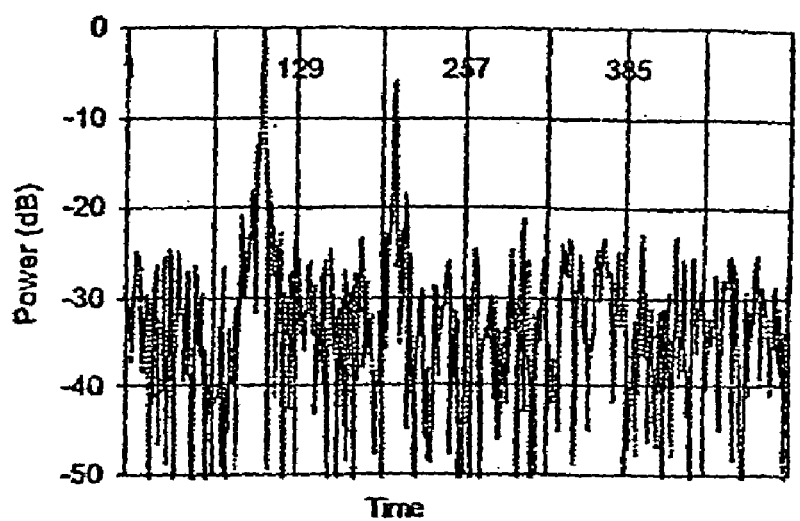
FIG. 11 demonstrates the use of a linear FM pulse coding technique as in FIG. 10 for a TBP of 800.

A plot of the original case with a TBP of 200 is shown in FIG. 10 and the new case with a TBP of 800 is shown in FIG. 11. The increase of the time bandwidth product has increased the coding gain sufficiently enough that the third and weakest pulse is now visible above the noise floor. The coding gain was increased from 23.0 dB to 29.0 dB or an overall increase 6.0 dB. In both plots, the power has been normalised to the peak located at sample 100. The drop in the noise floor in going from a TBP of 200 to 800 is readily apparent.

Figure 12:
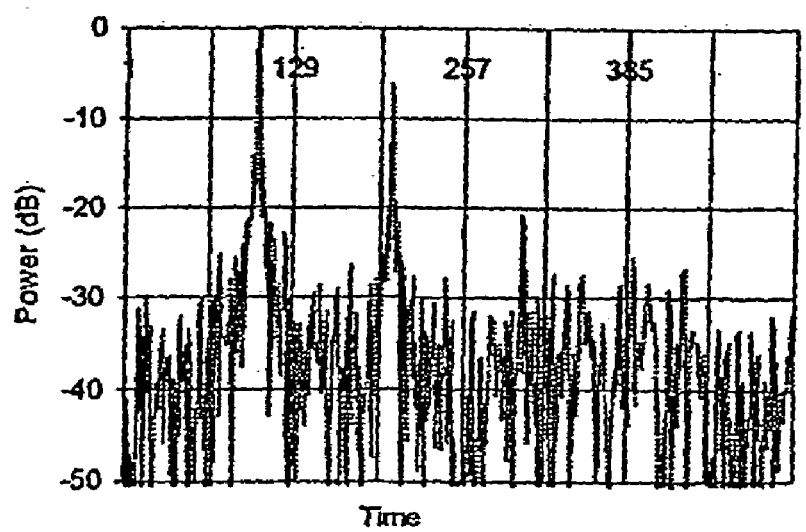
FIG. 12 demonstrates the use of a linear FM pulse coding technique as in FIG. 10 for a TBP of 2250.
Figure 13:
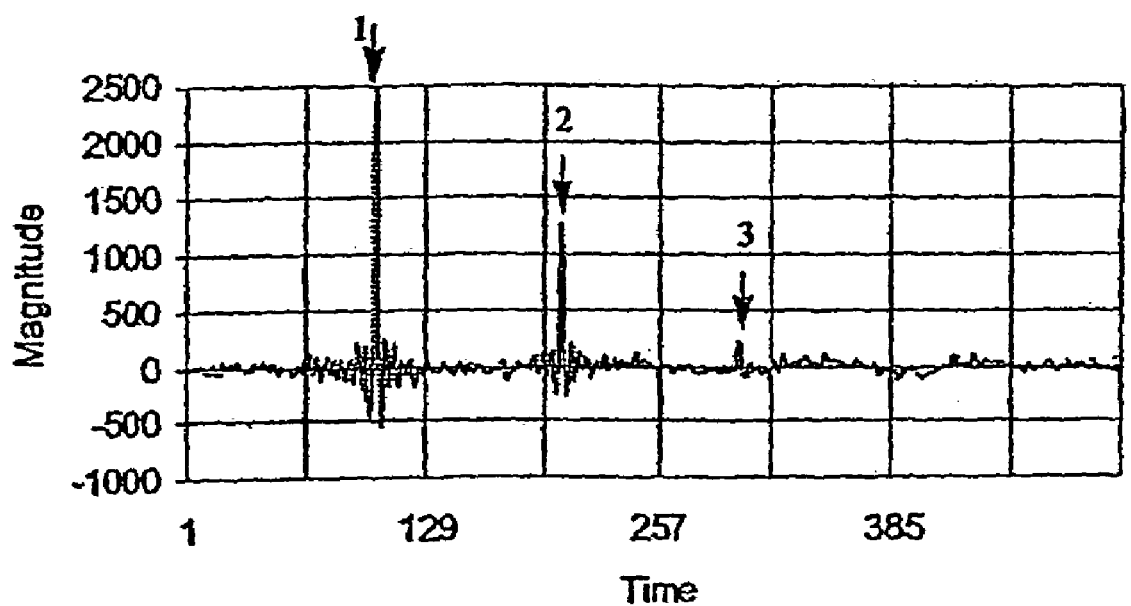
FIG. 13 is a time domain plot for the case of a TBP of 2250, where the detector amplitude was plotted.

To further make this point, a plot for the case of a TBP of 2250 is shown in FIG. 12. In order to compare this high time bandwidth product detection scheme to the other coding techniques, a time domain magnitude plot where the detector amplitude has been plotted is shown in FIG. 13. The noise amplitude should be suppressed by $\sqrt{2250}$, or about 47.4. The peak amplitude of pulse 1 is 2505, pulse 2 is 1252 and pulse 3 is 250. The noise magnitude was the same as that for the signal for peak 1, therefore the noise magnitude should be suppressed to a level of approximately 52. As seen from FIG. 13, this is more or less the case. Due to the high level of noise suppression achieved, the signal for pulse 3 is quite visible relative to the noise background. This is readily apparent when the TBP=375 case in FIG. 9 where pulse 3 is not visible, is compared with the TBP=2250 case in FIG. 13 where pulse 3 is visible.

Higher Time Bandwidth Products can be used to achieve higher coding gains, however these may be limited depending on the means used to achieve the signal coding. A mechanical chopper would be limited by the ability to replicate the linear FM code onto the chopper wheel, whereas acoustic-optic modulators could achieve much higher TBP's but at much higher expense.

Scanning Methodologies

For manual scanning, the probe is moved manually across the surface to be analyzed, and analyzes only the area immediately under observation. The spectral characteristics are observed at a fixed point in space $(x_0, y_0)$. Thus, one obtains a one-dimensional plot of the spectral response for each point $(x_0, y_0)$. This mode of operation is useful if the fluorescing material is diffusely distributed throughout the medium to be observed, or if localized analysis is required.

For two-dimensional scanning, the fluid flows through a chamber and spectral responses are obtained for each point in time $(t, \lambda)$. This mode of operation is useful if the fluorescing material is periodic as in an open system such as a municipal water system or a closed system for fluid processing.

For three-dimensional scanning, quantitative and qualitative data can be obtained for closed loop feedback control and detection of physical and optical characteristics in subject matter. As the probe is scanned across a two-dimensional surface, spectral responses are obtained for each point $(x_i, y_i, z_i, \lambda)$.

To gain a better understanding of the invention described herein, the following examples are set forth. It should be understood that these examples are for illustrative purposes only. Therefore; they should not limit the scope of this invention in any way.

EXAMPLES

Example I

Optical System for Analyzing Fluid Samples

In one embodiment of the present invention, the optical system can be designed to perform the analysis of fluid samples, for example for the detection of turbidity and/or bio-mass in a flowing water sample. This form of the invention may also be used for the analysis of a petroleum sample, for example. In this embodiment of the optical system the change(s) in the spectral properties of a test sample are detected and evaluated.

Figure 16:
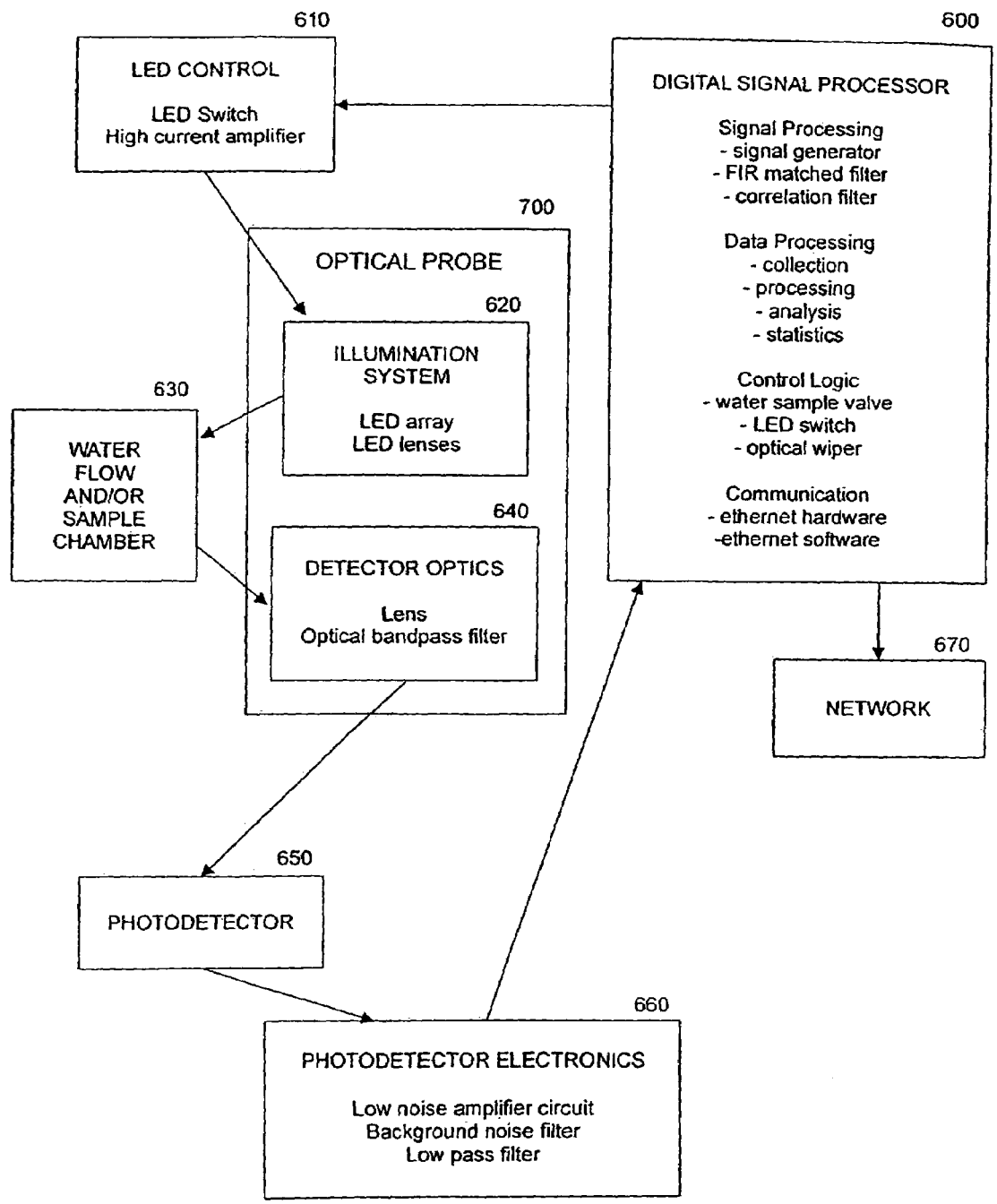
FIG. 16 illustrates an optical system that can be used for the testing of water quality, according to one embodiment of the present invention.

An embodiment of the invention a system used for this purpose is illustrated in FIG. 16. This example is directed towards water analysis, however it may equally well be used for the analysis of other fluids. The optical system comprises a digital signal processor 600, a LED control system 610, an illumination system 620, a sample chamber or water flow 630 into which the optical probe 700 may be placed, detector optics 640, a photodetector 650, photodetector electronics 660 and a network 670 to which the DSP 600 is connected. The optical probe 700 which can be inserted into the flowing water comprises both the illumination system 620 and the detector optics 640 which can be aligned in order to maximise the detection of radiation emitted by the water sample upon it illumination.

The digital signal processor 600 comprises software and hardware integrated together to enable it to perform tasks including signal processing, data processing, system control through the use of control logic and communication with an external network for example the Internet or a local area network (LAN). The signal processing performed by the DSP includes the operation of the signal generator enabling the encoding of the illumination signal (radiation). In addition, the signal processing enabled by the DSP includes the FIR matched filtering and the correlation filtering of the received light signal (detected radiation emitted by the water sample). The data processing performed by the DSP can include the collection, processing and analysis of the collected data. A statistical analysis of the data may also be performed by the DSP in order to determine for example return periods of particular levels of detected radiation. The control of a valve for withdrawing a sample from a water flow into a sample chamber and the control of the LED switch thereby controlling the activation of a LED, are both provided by the control logic incorporated into the DSP. The control logic may additionally control an optical wiper that can be used to remove bio-fouling which may collect and grow on the optical probe. The inclusion of an optical wiper may reduce the frequency of the removal of the probe from the sample chamber or water flow, for cleaning. The DSP further comprises a communication system which enables it to connect with a network thereby enabling the transmission of the collected information to other sites without the need for personnel to visit the test site for data retrieval. In the present embodiment, this communication is provided by software and hardware which enables an ethernet link to be created.

The LED control 610 includes the LED switch and a high current amplifier, wherein the LED switch activates the desired LED and the high current amplifier transforms the available power supply to a level which is compatible with the activation of a LED to a desired intensity level.

The optical probe 700 comprises both the illumination system 620 and the detector optics 640 wherein this probe can be inserted into the water flow directly or into a sample chamber containing water extracted from the water flow. If the probe is inserted into the moving water flow, the shape of the probe should be designed for minimal disruption of the water flow. The illumination system comprises a LED array and LED optics for focusing the photonic radiation generated by the LED array. The LED array may be a single diode or may be a collection of diodes thereby spanning a predetermined band of wavelengths. In one embodiment, a green and blue light emitting diode is used in the optical system. The detector optics comprise lens for collecting the radiation emitted by the water sample in addition to an optical bandpass filter for pre-filtering the collected radiation before it is detected by the photodetector 650 for conversion of the detected radiation into an electronic signal.

The photodetector electronics 660 comprise a collection of filters which pre-filter the collected information prior to its processing by the DSP, for example the match filtering of the collected information relating to the water samples illumination.

In this embodiment of the invention, the DSP is a stand-alone system which may include an internal power supply or a power converter in order for the DSP to be interconnected to a standard AC power source, for example a wall socket. In addition, this stand-alone type of system enables the deployment of this optical system at a plurality of sites, for example at various locations in a water supply system. Through the interconnection of this collection of optical systems to a communication network, for example the Internet or a local area network, the information which is collected and processed by these optical systems can be transmitted to a central site, without the need for personnel to visit each test site to collect the information. This type of system may provide a means for efficiently and cost effectively evaluating a water supply system.

This optical system is capable of detecting reflectance and fluorescence, wherein reflectance is indicative of the turbidity of the water sample and the fluorescence is indicative of the bio-matter contained within the water sample. It is known to a worker skilled in the art that bio-matter, upon its illumination will fluoresce and the detection of the intensity of fluorescence can potentially enable the determination of the level of bio-matter within a water system. This embodiment of the optical system evaluates the changes in the reflectance and the fluorescence within the water flow, thereby potentially being able to identify situations which may be of particular relevance. In this manner, upon the detection of a particular level of change in the optical signature of the water flow, the DSP may be able to activate a sampling procedure, wherein a sample of the water flow is collected for laboratory analysis. This type of almost constant testing and selective laboratory analysis can potentially reduce the cost of monitoring a water supply system and increase the identification of a potential problem.

Figure 17:
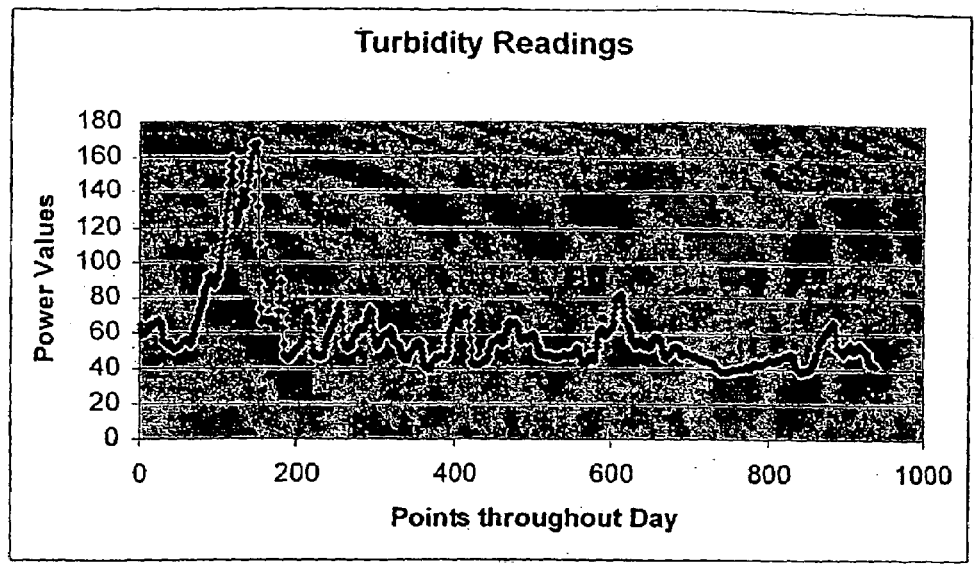
FIG. 17 is a plot of the turbidity readings for a water test site that were obtained using the optical system illustrated in FIG. 16.
Figure 18:
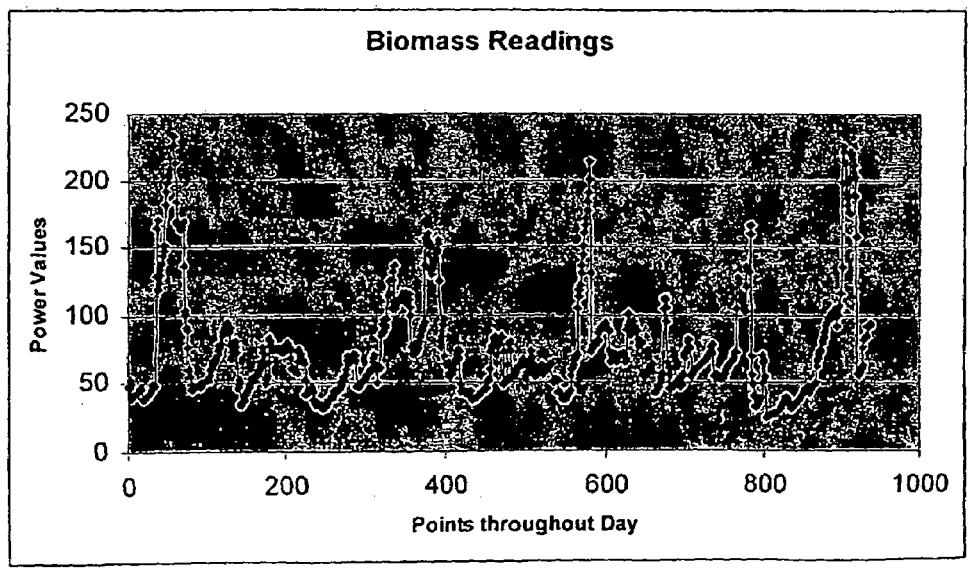
FIG. 18 is a plot of the biomass readings for a water test site that were obtained using the optical system illustrated in FIG. 16.

For example, FIG. 17 illustrates in a graphical format, the turbidity readings which are collected over the course of a day as collected by this optical system. FIG. 18 illustrates the bio-mass reading which are detected by the optical system also over the course of a day.

Example II

Spectrometer Incorporating a Matched Filter Receiver

Figure 14:
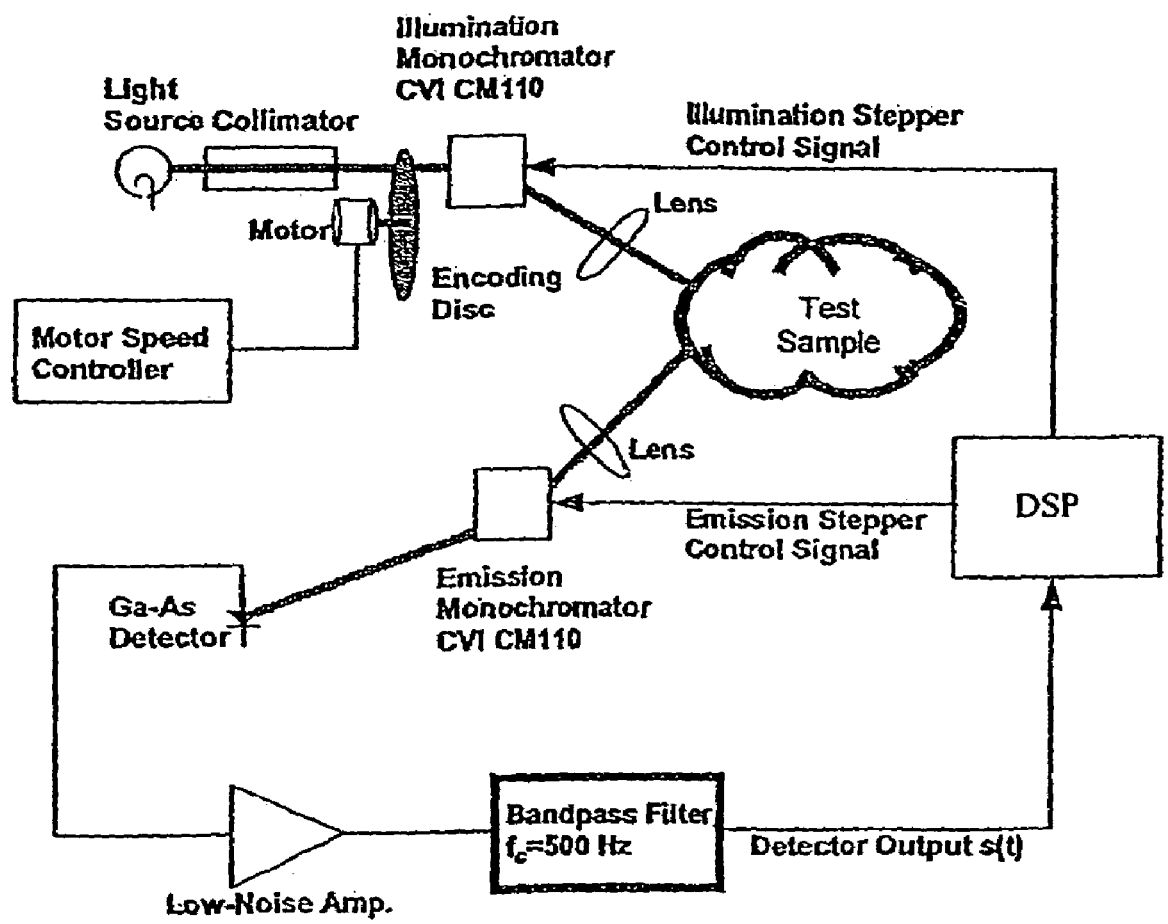
FIG. 14 is a schematic representation of a spectrometer that incorporates a matched filter receiver.
Figure 15:
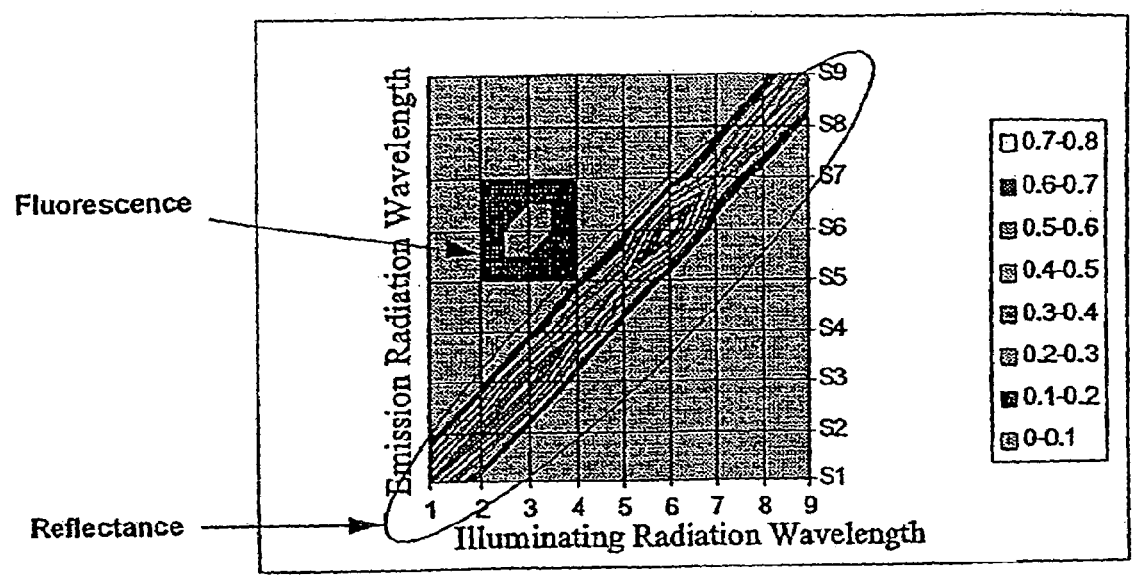
FIG. 15 shows a detector output, recorded for $\lambda_i$, and $\lambda_e$, from the spectrometer of FIG. 14 and plotted for display.

One embodiment is shown in FIG. 14 comprising a light source, for example, a miniature Xenon bulb that has an emission spectrum approximately equal to that of a 6000° K Blackbody with a few discrete spectral lines. The light is collimated and modulated by a chopper wheel, which provides a 500 Hz On-Off modulation to the light entering the illumination monochromator. The illumination monochromator operating under the control of the CPU sweeps the illumination wavelength from 250 nm to 800 nm in steps of 10 nm. This illumination is focused onto the area of interest. The received light monochromator operating under the control of the CPU sweeps the received light wavelength from 250 nm to 800 nm in steps of 10 nm. It is controlled in such a way that for every illumination wavelength sample $\lambda_i$, it sweeps over the range of wavelengths greater than or equal to $\lambda_i$. A Ga-As photodiode is used as the optical detector, with the signal from the photodiode being amplified by a low noise amplifier (LNA). The output of the LNA can be filtered using an analog filter, or it can be digitized using an analog to digital converter (ADC) and processed digitally using an IIR or FIR digital filter. The detector output is recorded for each $\lambda_i$ and $\lambda_e$, and can be plotted for display as shown in FIG. 15.

One important issue to be dealt with is the magnitude versus wavelength calibration of the system, since the Xenon Light source is not spectrally flat. This can be done using a standard diffuse reflection source, which is spectrally flat in an optical wavelength sense. The calibration factor can then be applied to the collected data such that the spectral colouring of the illumination source can be removed from the data. This process is essentially spectral equalization of the data.

Once the data is equalized, it can be displayed in a number of ways such as contour plots, surface plots, for example, enabling easy visualization of the illumination/emission spectra. This may require some normalization to say the strongest spectral peak of some response at a fixed wavelength location. This will have to be determined experimentally. An example of a surface type of plot is shown in FIG. 15.

Example III

One embodiment of this invention comprises an optical system comprises: a) a light emitting diode (LED), as the illumination light source, which is controlled by the digital signal processing means to emit a radiation bandwidth ranging from 380 to 500 nanometers; b) a stepper motor controlled, grating illumination monochromator which is controlled by the digital signal processing means to receive light from the illumination device and to deliver the $N^{th}$ wavelength in a pulse sequence; c) an optical fibre probe that is coupled to the monochromator with collimating and focusing elements that delivers the $N^{th}$ wavelength to a subject area. This optical probe is located in an assembly that orients the illumination optics with that of the detecting optics such that they are at a constant angle to each other; d) collecting means for gathering the resultant radiation of the $N^{th}$ wavelength and delivering the information via light collection lenses and fibre coupled to a stepper motor controlled, grating detection monochromator; and e) a photodetector such as a Ga—As integrated photodiode and amplifier. The stepper motor controlled, grating monochromators (both the illumination and detection monochromators) are controlled by the digital signal processing means to perform tasks to pass the $N^{th}$ wavelength reactive characteristics at a specific time.

Typically a Ga—As integrated photodiode and amplifier is made up of stock electronic components that consist of a photodiode and transimpedance amplifier on the same chip. This is sampled by the digital signal processing means to sense the radiation at a specific time. A photodiode is used as an optical detector, with the signal from the photodiode being amplified by a low noise amplifier (LNA). The output of the LNA is filtered using an analog filter to condition the signal from the photodetector with an op amp, amplifying the signal to a specific range and is digitised using an analog to digital converter (ADC) and processed digitally using an FIR digital filter and a digital signal coding software technique such that a time/bandwidth product can be measured using a correlation receiver.

The system further comprises a DSPS device where an illumination modulation coding signal is created using a 32 bit linear FM pulse coding technique for pulse compression, the detection pulse coding is resolving the time bandwidth product with a matched correlation receiver, and the detection of specific amplitudes of irradiance can prompt the DSPS to run a specific routine to test for specific signal response characteristics in this case fluorescence and reflectance can be measured depending on the limitations of the wavelengths of illumination. The monochromator gratings can operate through the visible spectrum and can be substituted for other wavelengths into the UV or IR ; and a digital signal processing technique such that software that recognises the peaks of data and their rule based weighted relevance can control the illuminator and detector monochromators.

Example IV

In one embodiment of the present invention an optical system can be designed with the ability to control the wavelength of the scan (illumination radiation) including modulation techniques. This type of optical system can provide maximum optical flexibility, which can be required for applications including research and diagnostics.

An embodiment of the optical system designed for this scenario comprises: a digital signal processing means which is integrated into a computing device with the emitter control electronics comprising pulse code software to create a synchronous pulse for direct modulation of the optical emission processing means frequency and the received signal processing means incorporating a signal correlation match filter; a flashlamp providing the photonic energy source; optical emission processing means incorporating a frequency modulator circuit for modulating the illumination radiation, a refractive or diffractive optical system whereby the optical centre wavelength is chosen by the use of a position controller to move the fixed light conditioning optics of the emitter optical system; received light optical processing means incorporating a refractive or diffractive optical system whereby the optical centre wavelength is chosen by the use of a position controller to move the fixed light conditioning optics of the detector optical system; and a silicon APD photodetector acting as the optical detector.

In this embodiment, correction of the emitted spectrum for a flashlamp may require more than simply comparing it to a standard diffuse reflection source as in Example II. Highly specific wavelengths of peak emissions may require adjustment of apertures and detection system gains in order to maintain accurate signal to noise ratio normalisation. These adjustments are ideally made automatically and recorded as a data variable in the normalisation process. This is especially the case where sample absorption and reflection is highly variable at the peak emitter wavelengths. A system that is set for maximum fluorescence detection at non-peak wavelengths could easily be over saturated by the response by the peak wavelength.

Example V

In one embodiment of the present invention an optical system can be designed for maximum sensitivity of resultant radiation resulting from the illumination of a test sample by a known wavelength of light. This type of optical system can be useful for fluorescence analysis, especially if a spectral probe is attached to the subject of interest and has know spectral properties such that detection of a specific wavelength of fluorescence, absorption or reflection can be measured.

An embodiment of the optical system designed for this scenario comprises: a digital signal processing means which is integrated into a computing device with the emitter control electronics comprising pulse code software to create a synchronous pulse for direct modulation of the optical emission processing means frequency and the received signal processing means incorporating a signal correlation match filter; a laser providing the photonic energy source; optical emission processing means incorporating an acousto-optic scanner and a fixed emitter optical system; received light optical processing means incorporating fixed light conditioning optics; and a photomultiplier acting as the optical detector. This embodiment of the system can be used for direct sensing of specific fluorescence response from biomolecules within a test sample or subject matter.

Example VI

In a further embodiment of the present invention an optical system, which can be used in the lowest cost applications of fluorometry and reflectometry including for example particle measurement such as water turbidity. In this example, the optical device can be designed to illuminate a test sample with a specific wavelength of light and can detect the reflection of the same or a different wavelength or waveband reflected, or emitted by stimulation of the particles in the fluid.

An embodiment of the optical system associated with this type of device comprises: a stand alone digital signal processing means with the emitter control electronics comprising a pulse code software to create a synchronous pulse for the direct modulation of the optical emission processing means amplitude and the received signal processing means comprising a signal correlation matched filter; a light emitting diode (LED) acting as the photonic energy source; optical emission processing means comprising an amplitude modulator circuit and a fixed light conditioning emitter optical system; received light optical processing means incorporating a fixed light conditioning detector optical system and a silicon photodiode acting as the optical detector.

In this embodiment, the optical system emits directly into the fluid and the detector receives light from within the fluid. This is achieved by means of an optical fibre or by direct insertion of the optical system into the subject fluid. This type of procedure will reduce the reflection effects of the surface boundary layers, thereby potentially improving the signal to noise characteristics of the optical system.

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A system for performing an optical analysis of a test sample comprising:
   a) a photonic energy source for emitting electromagnetic radiation, wherein said photonic energy source is controlled by a digital signal processing means;
   b) an optical emission processing means for receiving electromagnetic radiation from the photonic energy source and transmitting one or more illumination wavelengths to a test sample, wherein the optical emission processing means is controlled by the digital signal processing means;
   c) a received light optical processing means for collecting and isolating one or more wavelengths of received electromagnetic radiation from the test sample and transmitting the isolated one or more wavelengths of received electromagnetic radiation to an optical detector, wherein said received light optical processing means is controlled by the digital signal processing means;
   d) an optical detector for sensing and converting the isolated one or more wavelengths of received electromagnetic radiation into an electrical signal; and
   e) digital signal processing means for performing matched filtering of the electrical signal received from the optical detector and for controlling the functionality of the photonic energy source, the optical emission processing means and the received light optical processing means, said digital signal processing means encoding the electromagnetic radiation prior to illumination of the test sample and said match filtering being performed by a filter correlated with the encoded electromagnetic radiation.

2. The system for performing an optical analysis of a test sample according to claim 1, wherein the encoding is performed using a modulation technique selected from the group comprising pulse amplitude modulation, pulse frequency modulation, pulse width modulation, binary phase shift keying or a function generator.

3. The system for performing an optical analysis of a test sample according to claim 1, wherein the digital signal processing means is a stand-alone system.

4. The system for performing an optical analysis of a test sample according to claim 1, wherein the digital signal processing means is a circuit board which is integrated into a computing system.

5. The system for performing an optical analysis of a test sample according to claim 3, wherein the digital signal processing means is capable of interconnection with a communication network, said communication network being selected from the group comprising local area network, wide area network, wireless network, the Internet or ethernet.

6. The system for performing an optical analysis of a test sample according to claim 1, wherein the photonic energy source is selected from the group comprising a laser, a laser diode, a light emitting diode, an arc flashlamp or a continuous wave bulb.

7. The system for performing an optical analysis of a test sample according to claim 1, wherein optical emission processing means and the received light optical processing means include one or more optical devices selected from the group comprising condensers, focusing devices, lenses, fibre optics; apertures and monochromators.

8. The system for performing an optical analysis of a test sample according to claim 1, wherein the optical detector is selected from the group comprising a gallium-arsenide photodiode, a cadmium sulfide photodiode or a silicon avalanche diode.

9. A system for performing an optical analysis of a fluid comprising:
   a) an optical probe including an illumination system including a photonic energy source for emitting electromagnetic radiation and optical devices for directing said electromagnetic radiation towards a fluid sample, said optical probe further including detector optics for collecting and directing electromagnetic radiation emitted by the fluid sample towards a photodetector, wherein said optical probe is inserted into a fluid flow or a sample chamber containing the fluid sample;
   b) a control means for activating the photonic energy source;
   c) a photodetector for sensing and converting the electromagnetic radiation emitted by the fluid sample into an electrical signal; and
   d) a digital signal processing means for performing matched filtering of the electrical signal received from the photodetector, said digital signal processing means further controlling the activation of the photonic energy source, said digital signal processing means encoding the electromagnetic radiation prior to illumination of the fluid sample and said match filtering being performed by a filter correlated with the encoded electromagnetic radiation.

10. The system for performing an optical analysis of a fluid according to claim 9, wherein the encoding is performed using a modulation technique selected from the group comprising pulse amplitude modulation, pulse frequency modulation, pulse width modulation, binary phase shift keying or a function generator.

11. The system for performing an optical analysis of a fluid according to claim 9, wherein the digital signal processing means is a stand-alone system.

12. The system for performing an optical analysis of a fluid according to claim 9, wherein the digital signal processing means is a circuit board which is integrated into a computing system.

13. The system for performing an optical analysis of a fluid according to claim 9, wherein the digital signal processing means is capable of interconnection with a communication network, said communication network being selected from the group comprising a local area network, wide area network, wireless network, an ethernet or the Internet.

* * * * *